(12) United States Patent
Pendri et al.

(10) Patent No.: US 7,517,900 B2
(45) Date of Patent: Apr. 14, 2009

(54) PYRAZOLE DERIVATIVES AS CANNABINOID RECEPTOR MODULATORS

(75) Inventors: Annapurna Pendri, South Glastonbury, CT (US); Samuel Gerritz, Guilford, CT (US); Dharmpal S. Dodd, Princeton, NJ (US); Chongqing Sun, East Windsor, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 486 days.

(21) Appl. No.: 10/959,866

(22) Filed: Oct. 6, 2004

(65) Prior Publication Data
US 2005/0080087 A1   Apr. 14, 2005

Related U.S. Application Data

(60) Provisional application No. 60/510,445, filed on Oct. 10, 2003.

(51) Int. Cl.
*A61K 31/415* (2006.01)
*C07D 231/00* (2006.01)

(52) U.S. Cl. .................... 514/404; 548/356.1
(58) Field of Classification Search ............. 514/404; 548/356.1
See application file for complete search history.

(56) References Cited

U.S. PATENT DOCUMENTS

| 5,420,141 | A | * | 5/1995 | Boigegrain et al. | 514/314 |
| 5,607,958 | A | * | 3/1997 | Boigegrain et al. | 514/406 |
| 5,616,592 | A | * | 4/1997 | Boigegrain et al. | 514/314 |
| 5,635,526 | A | * | 6/1997 | Boigegrain et al. | 514/406 |
| 5,744,491 | A | * | 4/1998 | Boigegrain et al. | 514/341 |
| 5,744,493 | A | * | 4/1998 | Boigegrain et al. | 514/359 |

FOREIGN PATENT DOCUMENTS

| EP | 0 337 944 | | 7/1993 |
| GB | 2 281 295 | | 3/1995 |
| JP | 10-7657 | | 1/1998 |
| WO | WO 92/02513 | | 2/1992 |
| WO | WO 96/23783 | | 8/1996 |
| WO | WO 00/76984 | | 12/2000 |
| WO | WO 01/62233 | | 8/2001 |
| WO | WO 01/90078 | | 11/2001 |
| WO | WO 02/066480 | | 8/2002 |
| WO | WO 02/076438 | | 10/2002 |
| WO | WO 02/088084 | | 11/2002 |
| WO | WO 03/051850 | | 6/2003 |
| WO | WO 03/051851 | | 6/2003 |
| WO | WO2004/089931 | A1 | 10/2004 |
| WO | WO2004/089932 | A1 | 10/2004 |

OTHER PUBLICATIONS

Herrero, et al (Tetrahedron, 58 (2002) 8581-8589).*
Duarte, Exp. Neur., 204(2007) 479-484, esp. pp. 479.*
Sarabu, Exp. Opin., (2003) 12(10), 1721-1726, esp. 1721.*
Herrero, et al., Tetrahedron, 58, 2002, 8581-8589.*
Ambrogi, V. et al., "New Oral Antidiabetic Drugs, Part I", Arzneim.-Forsch. (Drug Res.), vol. 21, No. 2, pp. 200-204 (1971).
Bicking, J.B. et al., "Pyrazine Diruetics. III. 5- and 6-Alkyl, -Cycloalkyl, and -Aryl Derivatives of N-Amidino-3-aminopyrazinecarboxamides", J. Med. Chem., vol. 10, No. 4, pp. 598-602 (1967).
Bonnet, V. et al., "Syntheses if substituted pyridines, quinolines and diazines via palladium-catalyzed cross-coupling of aryl Grignard reagents", Tetrahedron, vol. 58, pp. 4429-4438 (2002).
Colombo, G. et al., "Appetite Suppression and Weight Loss After the Cannabinoid Antagonist SR 141716", Life Sciences, vol. 63, No. 8, pp. PL113-PL117 (1998).
Di Marzo, V. et al, "Leptin-regulated endocannabinoids are involved in maintaining food intake", Nature, vol. 410, pp. 822-825 (2001).
Galiègue, S. et al., "Expression of central and peripheral cannabinoid receptors in human immune tissues and leukocyte subpopulations", Eur. J. Biochem., vol. 232, pp. 54-61 (1995).
Glass, M. et al., "Cannabinoid Receptors in the Human Brain: A Detailed Anatomical and Quantitative Autoradiographic Study in the Fetal, Neonatal and Adult Human Brain", Neuroscience, vol. 77, No. 2, pp. 299-318 (1997).
Hildebrandt, A.L. et al., "Antiobesity effects of chronic cannabinoid $CB_1$ receptor antagonist treatment in diet-induced obese mice", European Journal of Pharmacology, vol. 462, pp. 125-132 (2003).

(Continued)

*Primary Examiner*—Rei-tsang Shiao
*Assistant Examiner*—Susannah Chung
(74) *Attorney, Agent, or Firm*—Maureen S. Gibbons

(57) ABSTRACT

The present application describes compounds according to Formula I, wherein A, B, E, $R^1$, $R^2$, $R^3$, $R^4$, Y and Z are described herein. Additionally, the present application describes pharmaceutical compositions comprising at least one compound according to Formula I and optionally one or more additional therapeutic agents. Finally, the present application describes methods of treatment using the compounds according to Formula I both alone and in combination with one or more additional therapeutic agents.

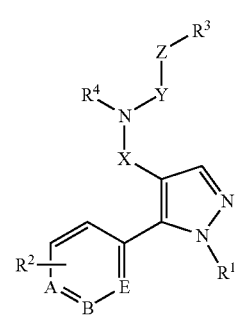

32 Claims, No Drawings

OTHER PUBLICATIONS

Hutchinson, J.H. et al., "Substituted Thiopyrano[2,3,4,-c,d]indoles as Potent, Selective, and Orally Active Inhibitors of 5-Lipoxygenase. Synthesis and Biological Evaluation of L-691,816", J. Med. Chem., vol. 36, No. 19, pp. 2771-2787 (1993).

Matsuda, L.A. et al., "Structure of a cannabinoid receptor and functional expression of the cloned cDNA", Nature, vol. 346, pp. 561-564 (1990).

Munro, S. et al., "Molecular characterization of a peripheral receptor for cannabinoids", Nature, vol. 365, pp. 61-65 (1993).

Nelson, P.J. et al., "1,2,4-Triazoles. VI. The Synthesis of Some-s-Triazolo[4,3-a ]pyrazines", J. Org. Chem., vol. 27, pp. 3243-3248 (1962).

Reinecke, M.G. et al., "The α-Methylation of Pyridines by Primary Alcohols and Raney Nickel", Journal of the American Chemical Society, vol. 86, pp. 5355-5356 (1964).

Rowland, N.E. et al., "Effects of the cannabinoid receptor antagonist SR 141716, alone and in combination with dexfenfluramine or naloxone, on food intake in rats", Psychopharmacology, vol. 159, pp. 111-116 (2001).

Trillou, C.R. et al., "Anti-obesity effect of SR141716, a CB1 receptor antagonist, in diet-induced obese mice", Am. J. Physiol. Regul. Integr. Comp. Physiol., vol. 284, pp. R345-R353 (2003).

Williams, C.M. et al., "Anandamide induces overeating: mediation by central cannabinoid (CB1) receptors", Psychopharmacology, vol. 143, pp. 315-317 (1999).

* cited by examiner

PYRAZOLE DERIVATIVES AS CANNABINOID RECEPTOR MODULATORS

RELATED APPLICATIONS

This application claims priority benefit under Title 35 § 119(e) of U.S. provisional Application No. 60/510,445, filed Oct. 10, 2003, the contents of which are herein incorporated by reference.

BACKGROUND OF THE INVENTION

Delta-9-tetrahydrocannabinol or Delta-9 THC, the principle active component of *Cannabis sativa* (marijuana), is a member of a large family of lipophilic compounds (i.e., cannabinoids) that mediate physiological and psychotropic effects including regulation of appetite, immunosuppression, analgesia, inflammation, emesis, anti-nocioception, sedation, and intraocular pressure. Other members of the cannabinoid family include the endogenous (arachidonic acid-derived) ligands, anandamide, 2-arachidonyl glycerol, and 2-arachidonyl glycerol ether. Cannabinoids work through selective binding to and activation of G-protein coupled cannabinoid receptors. Two types of cannabinoid receptors have been cloned including CB-1 (L. A. Matsuda, et al., *Nature*, 346, 561-564 (1990)), and CB-2 (S. Munro, et al., *Nature*, 365, 61-65 (1993)). The CB-1 receptor is highly expressed in the central and peripheral nervous systems (M. Glass, et al., *Neuroscience*, 77, 299-318 (1997)), while the CB-2 receptor is highly expressed in immune tissue, particularly in spleen and tonsils. The CB-2 receptor is also expressed on other immune system cells, such as lymphoid cells (S. Galiegue, et al., *Eur J Biochem*, 232, 54-61 (1995)). Agonist activation of cannabinoid receptors results in inhibition of cAMP accumulation, stimulation of MAP kinase activity, and closure of calcium channels.

There exists substantial evidence that cannabinoids regulate appetitive behavior. Stimulation of CB-1 activity by anandamide or Delta-9 THC results in increased food intake and weight gain in multiple species including humans (Williams and Kirkham, *Psychopharm.*, 143, 315-317 (1999)). Genetic knock-out of CB-1 result in mice that were hypophagic and lean relative to wild-type litter mates (DiMarzo, et al., *Nature*, 410, 822-825 (2001)). Published studies with CB-1 small molecule antagonists have demonstrated decreased food intake and body weight in rats (Trillou, et. al., *Am. J. Physiol. Regul. Integr. Comp. Physiol.*, R345-R353, (2003)). Chronic administration of the CB-1 antagonist AM-251 for two weeks resulted in substantial body weight reduction and decreased adipose tissue mass (Hildebrandt, et. al., *Eur. J. Pharm*, 462, 125-132 (2003)). There are multiple studies that have assessed the anorexic effect of the Sanofi CB-1 antagonist, SR-141716 (Rowland, et. al., *Pyschopharm.*, 159, 111-116 (2001); Colombo, et. al., *Life Sci.*, 63, 113-117 (1998)). There are at least two CB-1 antagonists in clinical trials for regulation of appetite, Sanofi's SR-141716 and Solvay's SLV-319. Published Phase IIb data reveal that SR-141716 dose-dependently reduced body weight in human subjects over a 16 week trial period. CB-1 antagonists have also been shown to promote cessation of smoking behavior. Phase II clinical data on smoking cessation were presented in September of 2002 at Sanofi-Synthelabo's Information meeting. This data showed that 30.2% of patients treated with the highest dose of SR-141716 stayed abstinent from cigarette smoke relative to 14.8% for placebo.

DETAILED DESCRIPTION OF THE INVENTION

The present application describes compounds according to Formula I, pharmaceutical compositions comprising at least one compound according to Formula I and optionally one or more additional therapeutic agents and methods of treatment using the compounds according to Formula I both alone and in combination with one or more additional therapeutic agents.

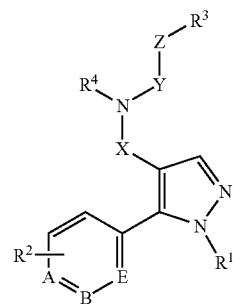

including all prodrugs, pharmaceutically acceptable salts and stereoisomers, wherein A, B, E, $R^1$, $R^2$, $R^3$, $R^4$, Y and Z are described herein.

DEFINITIONS

The following definitions apply to the terms as used throughout this specification, unless otherwise limited in specific instances.

As used herein, the term "alkyl" denotes branched or unbranched hydrocarbon chains containing 1 to 20 carbons, preferably 1 to 12 carbons, and more preferably 1 to 8 carbons, in the normal chain, such as, methyl, ethyl, propyl, isopropyl, butyl, sec-butyl, iso-butyl, tert-butyl, pentyl, hexyl, isohexyl, heptyl, 4,4-dimethylpentyl, octyl, 2,2,4-trimethylpentyl and the like. Further, alkyl groups, as defined herein, may optionally be substituted on any available carbon atom with one or more functional groups commonly attached to such chains, such as, but not limited to hydroxyl, halo, haloalkyl, mercapto or thio, cyano, alkylthio, heterocyclyl, aryl, heteroaryl, carboxyl, carbalkoyl, carboxamido, carbonyl, alkyl, alkenyl, alkynyl, nitro, amino, alkoxy, aryloxy, arylalkyloxy, heteroaryloxy, amido, and the like to form alkyl groups such as trifluoromethyl, 3-hydroxyhexyl, 2-carboxypropyl, 2-fluoroethyl, carboxymethyl, cyanobutyl and the like.

Unless otherwise indicated, the term "alkenyl" as used herein by itself or as part of another group refers to straight or branched chains of 2 to 20 carbons, preferably 2 to 12 carbons, and more preferably 2 to 8 carbons with one or more double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like. Further, alkenyl groups, as defined herein, may optionally be substituted on any available carbon atom with one or more functional groups commonly attached to such chains, such as, but not limited to halo, haloalkyl, alkyl, alkoxy, alkynyl, aryl, arylalkyl, cycloalkyl, amino, hydroxyl, heteroaryl, cycloheteroalkyl, alkanoylamino, alkylamido, arylcarbonylamino, nitro, cyano, thiol, alkylthio and/or any of the alkyl substituents set out herein.

Unless otherwise indicated, the term "alkynyl" as used herein by itself or as part of another group refers to straight or branched chains of 2 to 20 carbons, preferably 2 to 12 carbons and more preferably 2 to 8 carbons with one or more triple bonds in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl,3-undecynyl, 4-dodecynyl and the like. Further, alkynyl groups, as defined herein, may optionally be substituted on any available carbon atom with one or more functional groups commonly attached to such chains, such as, but not limited to halo, haloalkyl, alkyl, alkoxy, alkenyl, aryl, arylalkyl, cycloalkyl, amino, hydroxyl, heteroaryl, cycloheteroalkyl, alkanoylamino, alkylamido, arylcarbonylamino, nitro, cyano, thiol, alkylthio and/or any of the alkyl substituents set out herein.

Unless otherwise indicated, the term "cycloalkyl" as employed herein alone or as part of another group includes saturated or partially unsaturated (containing one or more double bonds) cyclic hydrocarbon groups containing 1 to 3 rings, appended or fused, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

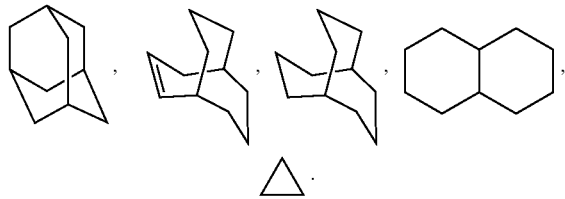

Further, any cycloalkyl may be optionally substituted through any available carbon atoms with one or more groups selected from hydrogen, halo, haloalkyl, alkyl, alkoxy, haloalkyloxy, hydroxyl, alkenyl, alkynyl, aryl, aryloxy, heteroaryl, heteroaryloxy, arylalkyl, heteroarylalkyl, alkylamido, alkanoylamino, oxo, acyl, arylcarbonylamino, amino, nitro, cyano, thiol and/or alkylthio and/or any of the alkyl substituents.

The term "cycloalkylalkyl" as used herein alone or as part of another group refers to alkyl groups as defined above having a cycloalkyl substituent, wherein said "cycloalkyl" and/or "alkyl" groups may optionally be substituted as defined above.

Unless otherwise indicated, the term "aryl" as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring, for example

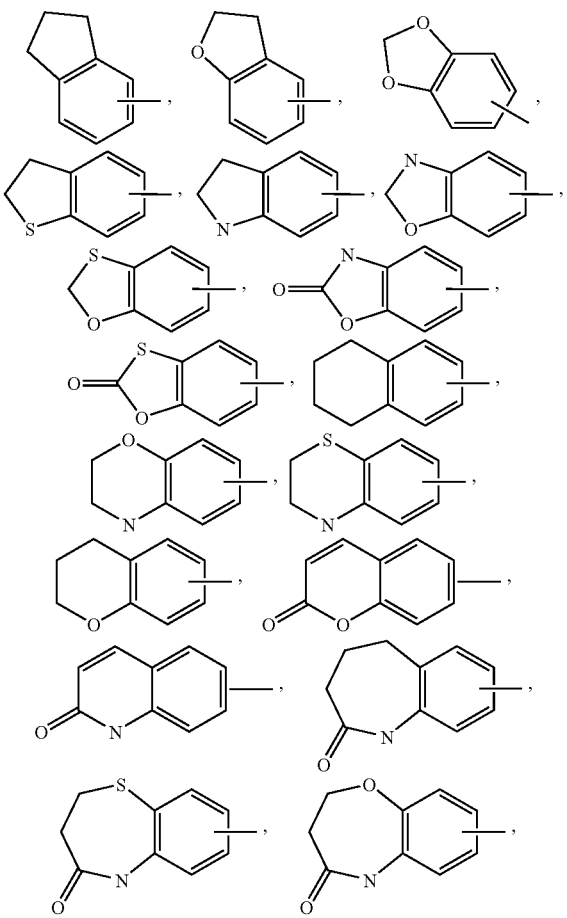

Further, "aryl", as defined herein, may optionally be substituted with one or more functional groups, such as halo, alkyl, haloalkyl, alkoxy, haloalkoxy, alkenyl, alkynyl, cycloalkyl, cycloalkylalkyl, heterocyclyl, heterocycloalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl and/or any of the alkyl substituents set out herein.

Unless otherwise indicated, the term "heteroaryl" as used herein alone or as part of another group refers to a 5- or 6-membered aromatic ring which includes 1, 2, 3 or 4 hetero atoms such as nitrogen, oxygen or sulfur. Such rings may be fused to an aryl, cycloalkyl, heteroaryl or heterocyclyl and include possible N-oxides as described in Katritzky, A. R. and Rees, C. W., eds. *Comprehensive Heterocyclic Chemistry: The Structure, Reactions, Synthesis and Uses of Heterocyclic Compounds* 1984, Pergamon Press, New York, N.Y.; and Katritzky, A. R., Rees, C. W., Scriven, E. F., eds. *Comprehensive Heterocyclic Chemistry II: A Review of the Literature*

1982-1995 1996, Elsevier Science, Inc., Tarrytown, N.Y.; and references therein. Further, "heteroaryl", as defined herein, may optionally be substituted with one or more substituents such as the substituents included above in the definition of "substituted alkyl" and "substituted aryl". Examples of heteroaryl groups include the following:

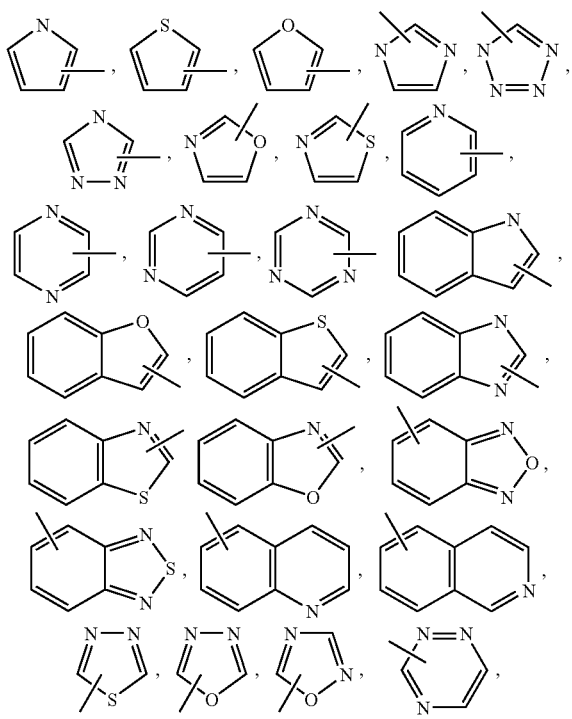

and the like.

The term "heteroarylalkyl" as used herein alone or as part of another group refers to alkyl groups as defined above having a heteroaryl substituent, wherein said heteroaryl and/or alkyl groups may optionally be substituted as defined above.

The term "heterocyclo", "heterocycle", "heterocyclyl" or "heterocyclic ring", as used herein, represents an unsubstituted or substituted stable 4 to 7-membered monocyclic ring system which may be saturated or unsaturated, and which consists of carbon atoms, with one to four heteroatoms selected from nitrogen, oxygen or sulfur, and wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but is not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isooxazolyl, isoxazolidinyl, morpholinyl, thiazolyl, thiazolidinyl, isothiazolyl, thiadiazolyl, tetrahydropyranyl, thiamorpholinyl, thiamorpholinyl sulfoxide, thiamorpholinyl sulfone, oxadiazolyl and other heterocycles described in Katritzky, A. R. and Rees, C. W., eds. *Comprehensive Heterocyclic Chemistry: The Structure, Reactions, Synthesis and Uses of Heterocyclic Compounds* 1984, Pergamon Press, New York, N.Y.; and Katritzky, A. R., Rees, C. W., Scriven, E. F., eds. *Comprehensive Heterocyclic Chemistry II: A Review of the Literature* 1982-1995 1996, Elsevier Science, Inc., Tarrytown, N.Y.; and references therein.

The term "heterocycloalkyl" as used herein alone or as part of another group refers to alkyl groups as defined above having a heterocyclyl substituent, wherein said heterocyclyl and/or alkyl groups may optionally be substituted as defined above.

The terms "arylalkyl", "arylalkenyl" and "arylalkynyl" as used alone or as part of another group refer to alkyl, alkenyl and alkynyl groups as described above having an aryl substituent. Representative examples of arylalkyl include, but are not limited to, benzyl, 2-phenylethyl, 3-phenylpropyl, phenethyl, benzhydryl and naphthylmethyl and the like.

The term "alkoxy", "aryloxy", "heteroaryloxy" "arylalkyloxy", or "heteroarylalkyloxy" as employed herein alone or as part of another group includes an alkyl or aryl group as defined above linked through an oxygen atom.

The term "halogen" or "halo" as used herein alone or as part of another group refers to chlorine, bromine, fluorine, and iodine, with bromine, chlorine or fluorine being preferred.

The term "cyano," as used herein, refers to a —CN group.

The term "methylene," as used herein, refers to a —CH$_2$— group.

The term "nitro," as used herein, refers to a —NO$_2$ group.

The compounds of formula I can be present as salts, which are also within the scope of this invention. Pharmaceutically acceptable (i.e., non-toxic, physiologically acceptable) salts are preferred. If the compounds of formula I have, for example, at least one basic center, they can form acid addition salts. These are formed, for example, with strong inorganic acids, such as mineral acids, for example sulfuric acid, phosphoric acid or a hydrohalic acid, with organic carboxylic acids, such as alkanecarboxylic acids of 1 to 4 carbon atoms, for example acetic acid, which are unsubstituted or substituted, for example, by halogen as chloroacetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as (C$_1$-C$_4$) alkyl or arylsulfonic acids which are unsubstituted or substituted, for example by halogen, for example methyl- or p-toluene-sulfonic acid. Corresponding acid addition salts can also be formed having, if desired, an additionally present basic center. The compounds of formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or trilower alkylamine, for example ethyl, tert-butyl, diethyl, diisopropyl, triethyl, tributyl or dimethyl-propylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds of formula I or their pharmaceutically acceptable salts, are also included.

Preferred salts of the compounds of formula I which contain a basic group include monohydrochloride, hydrogensulfate, methanesulfonate, phosphate, nitrate or acetate.

Preferred salts of the compounds of formula I which contain an acid group include sodium, potassium and magnesium salts and pharmaceutically acceptable organic amines.

The term "modulator" refers to a chemical compound with capacity to either enhance (e.g., "agonist" activity) or partially enhance (e.g., "partial agonist" activity) or inhibit (e.g., "antagonist" activity or inverse agonist activity) a functional property of biological activity or process (e.g., enzyme activity or receptor binding); such enhancement or inhibition may be contingent on the occurrence of a specific event, such as activation of a signal transduction pathway, and/or may be manifest only in particular cell types.

The term "prodrug esters" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates and the like.

Any compound that can be converted in vivo to provide the bioactive agent (i.e., the compound of formula I) is a prodrug within the scope and spirit of the invention.

Various forms of prodrugs are well known in the art. A comprehensive description of prodrugs and prodrug derivatives are described in:

*The Practice of Medicinal Chemistry*, Camille G. Wermuth et al., Ch 31, (Academic Press, 1996);

*Design of Prodrugs*, edited by H. Bundgaard, (Elsevier, 1985);

*A Textbook of Drug Design and Development*, P. Krogsgaard-Larson and H. Bundgaard, eds. Ch 5, pgs 113-191 (Harwood Academic Publishers, 1991).

Said references are incorporated herein by reference.

An administration of a therapeutic agent of the invention includes administration of a therapeutically effective amount of the agent of the invention. The term "therapeutically effective amount" as used herein refers to an amount of a therapeutic agent to treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration.

All stereoisomers of the compounds of the instant invention are contemplated, either in mixture or in pure or substantially pure form. The compounds of the present invention can have asymmetric centers at any of the carbon atoms including any one of the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic techniques, chiral HPLC or fractional crystallization.

The compounds of formula I of the invention can be prepared as shown in the following reaction schemes and description thereof, as well as relevant published literature procedures that may be used by one skilled in the art. Exemplary reagents and procedures for these reactions appear hereinafter and in the working Examples.

The following abbreviations are employed in the Schemes, Examples and elsewhere herein:

Ac=acetyl
AcCN=acetonitrile
AcOH=acetic acid
Boc=tert-butoxycarbonyl
BINAP=2,2'-bis(diphenylphosphino)-1,1'-binaphthyl
Brine=saturated aqueous sodium chloride solution
Chiralpak®=Trademark of Chiral Technologies, Inc. Eaton, Pa.
DCM=dichloromethane
DIPEA=N,N-diisopropylehtylamine
DMF=N,N-dimethylformamide
EDAC=1-(3-Dimethylaminopropyl)-3-ethylcarbodiimide hydrochloride
EtOAc=ethyl acetate
Et$_3$N=triethylamine
Et$_2$O=diethyl ether
Et$_3$SiH=triethylsilane
HOBt=1-hydroxybenzotriazole hydrate
HPLC=high performance liquid chromatography
LAH=lithium aluminum hydride
MeOH=methanol
MS or Mass Spec=mass spectrometry
NaB(OAc)$_3$H=sodium triacetoxyborohydride
NaOH=sodium hydroxide
NMM=N-methylmorpholine
PG=protecting group
PXPd=dichlorobis(chlorodi-tert-butylphosphine)palladium
RT=room temperature
TFA=trifluoroacetic acid
THF=tetrahydrofuran
THQ=tetrahydroquinoline
mp.=melting point
min=minute(s)
h=hour(s)
L=liter
mL=milliliter
µL=microliter
g=gram(s)
mg=milligram(s)
mol=moles
mmol=millimole(s)
nM=nanomolar

METHODS OF PREPARATION

Compounds of the present invention may be prepared by procedures illustrated in the accompanying schemes.

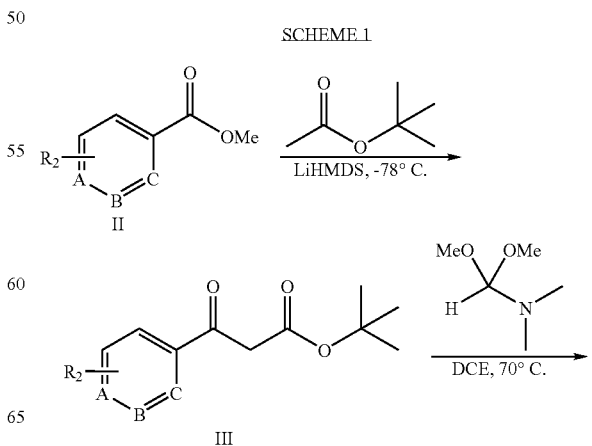

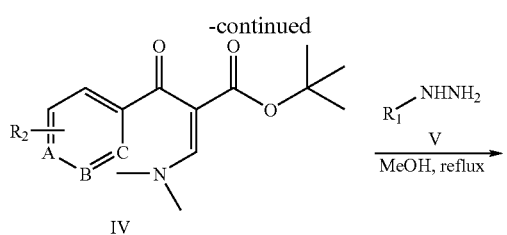

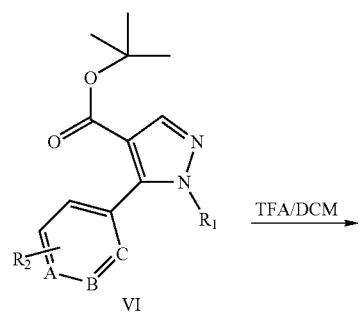

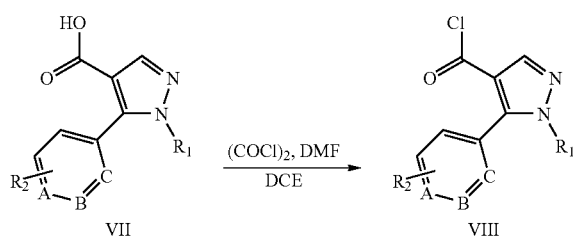

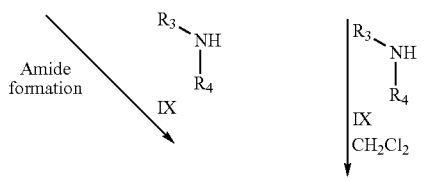

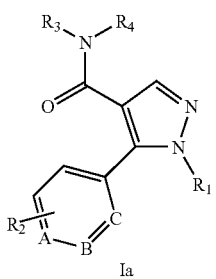

As illustrated in Scheme 1, compounds of formula Ia were prepared from intermediates of formula II. Intermediates of formula II can be obtained commercially, can be prepared by methods known in the literature, or can be readily prepared by one skilled in the art. In cases where A, B, or C are Nitrogen, intermediates of formula II can be prepared as described in the literature: (a) Bonnet, V.; et al. Tetrahedron 58, pp 4429-4438 (2002); (b) Hutchinson, J. H.; et al JACS, 36 pp 2771-2787 (1993); (c) Reinecke, M. G.; et al JACS 86 pp 5355-5356, (1964). Treatment of II with the lithium enolate of t-butyl acetate yields intermediates of formula III. Intermediates of formula III can also be obtained commercially. Treatment of intermediates of formula III with the dimethyl acetal of N,N-dimethylformamide affords intermediates of formula IV. Treatment of IV with intermediates of formula V affords intermediates of formula VI. Intermediates of formula V can be obtained commercially, can be prepared by methods known in the literature, or can be readily prepared by one skilled in the art. In some cases, intermediates of formula V are provided as their corresponding acid salts (e.g. HCl) and these are free-based prior to reaction with IV. The t-butyl ester protecting group of VI is removed with TFA in $CH_2Cl_2$ to afford intermediates of formula VII. Treatment of VII with a chlorinating agent such as oxalyl chloride yields intermediates of formula VIII. Treatment of VIII with a base and intermediates of formula IX provides compounds of formula Ia. Alternatively, compounds of formula Ia were prepared by treatment of VII with an amide-bond forming reagent (e.g. diisopropylcarbodiimide) and intermediates of formula IX. Intermediates of formula IX can be obtained commercially, can be prepared by methods known in the literature, or can be readily prepared by one skilled in the art.

SCHEME 2

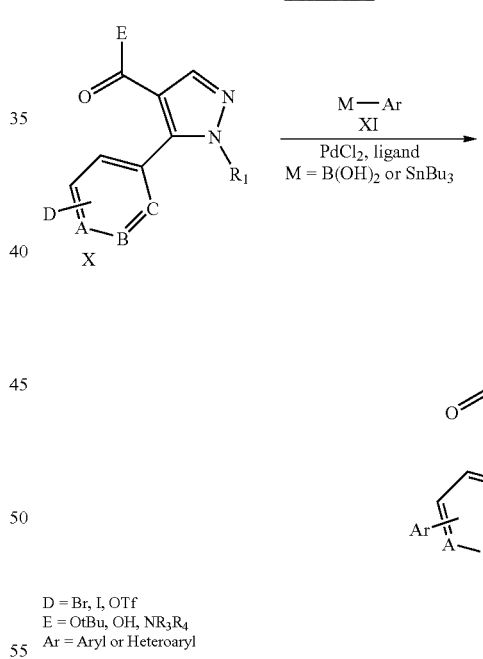

D = Br, I, OTf
E = OtBu, OH, $NR_3R_4$
Ar = Aryl or Heteroaryl

As illustrated in Scheme 2, compounds of formula XII were prepared by treatment of intermediates of formula X with the appropriate aryl or heteroaryl boronic acid or aryl or heteroaryl tin reagent of formula XI and a palladium catalyst. Compounds of formula XII represent compounds of formula Ia wherein E=$NR_3R_4$. Compounds of formula XII represent intermediates of formula VII wherein E=OtBu. Compounds of formula XII represent intermediates of formula VIII wherein E=OH.

SCHEME 3

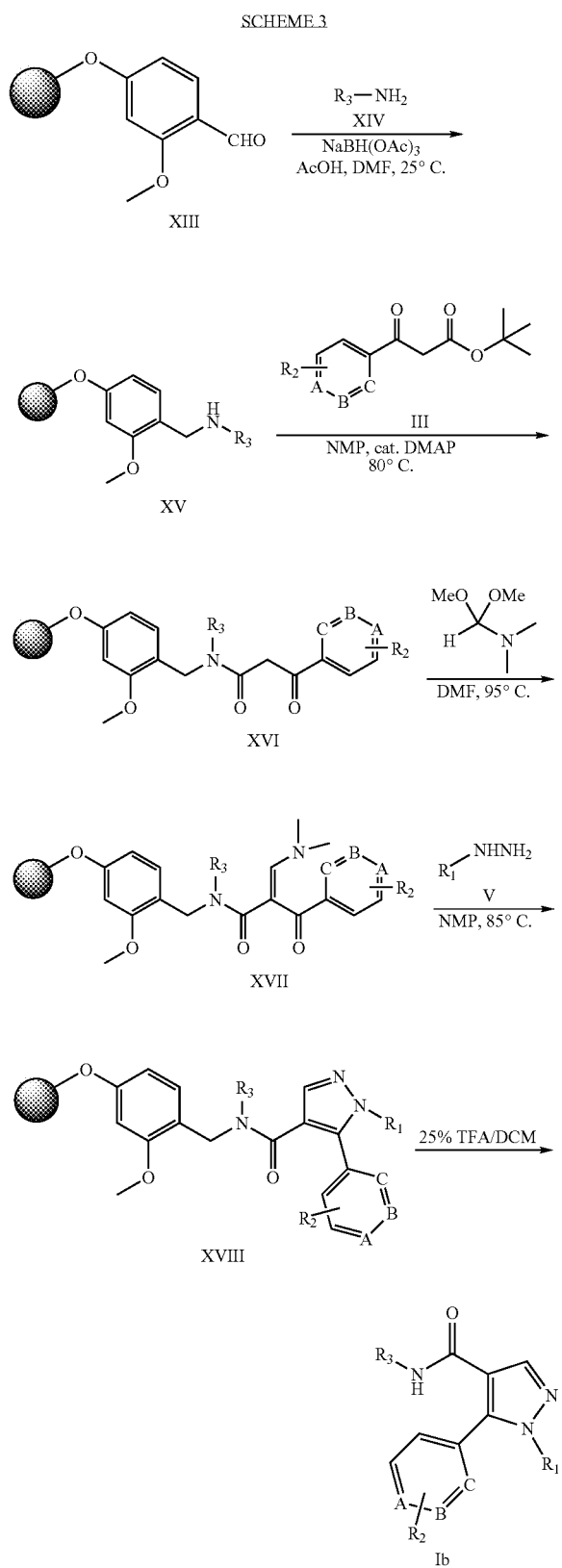

Compounds of formula Ib were prepared as described in Scheme 3. Treatment of solid-supported intermediates of formula XIII with intermediates of formula XIV provides solid-supported intermediates of formula XV. Solid-supported intermediates of formula XV can be obtained commercially, can be prepared by methods known in the literature, or can be readily prepared by one skilled in the art. Intermediates of formula XIV can be obtained commercially, can be prepared by methods known in the literature, or can be readily prepared by one skilled in the art. Treatment of XV with intermediates of formula III affords solid-supported intermediates of formula XVI. Intermediates of formula III can be prepared as described in Scheme 1, can be obtained commercially, can be prepared by methods known in the literature, or can be readily prepared by one skilled in the art. Treatment of XVI with the dimethyl acetal of N,N-dimethylformamide provides solid-supported intermediates of formula XVII. Treatment of XVII with intermediates of formula V affords solid-supported intermediates of formula XVIII. Intermediates of formula V can be obtained commercially, can be prepared by methods known in the literature, or can be readily prepared by one skilled in the art. In some cases, intermediates of formula V are provided as their corresponding acid salts (e.g. HCl) and these are free-based prior to reaction with XVII. Treatment of XVIII with trifluoroacetic acid in methylene chloride provides compounds of formula Ib.

SCHEME 4

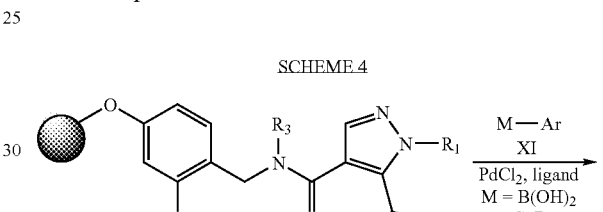

D = Br, I, OTf
Ar = Aryl or Heteroaryl

Compounds of formula Ic were prepared as illustrated in Scheme 4. Treatment of solid-supported intermediates of formula XIX with the appropriate aryl or heteroaryl boronic acid or aryl or heteroaryl tin reagent of formula XI and a palladium catalyst provided solid-supported intermediates of formula XX. Intermediates of formula XIX were prepared by analogy to the preparation of intermediates of formula XVIII as outlined in Scheme 3. Treatment of XX with trifluoroacetic acid in methylene chloride provides compounds of formula Ic.

SCHEME 5

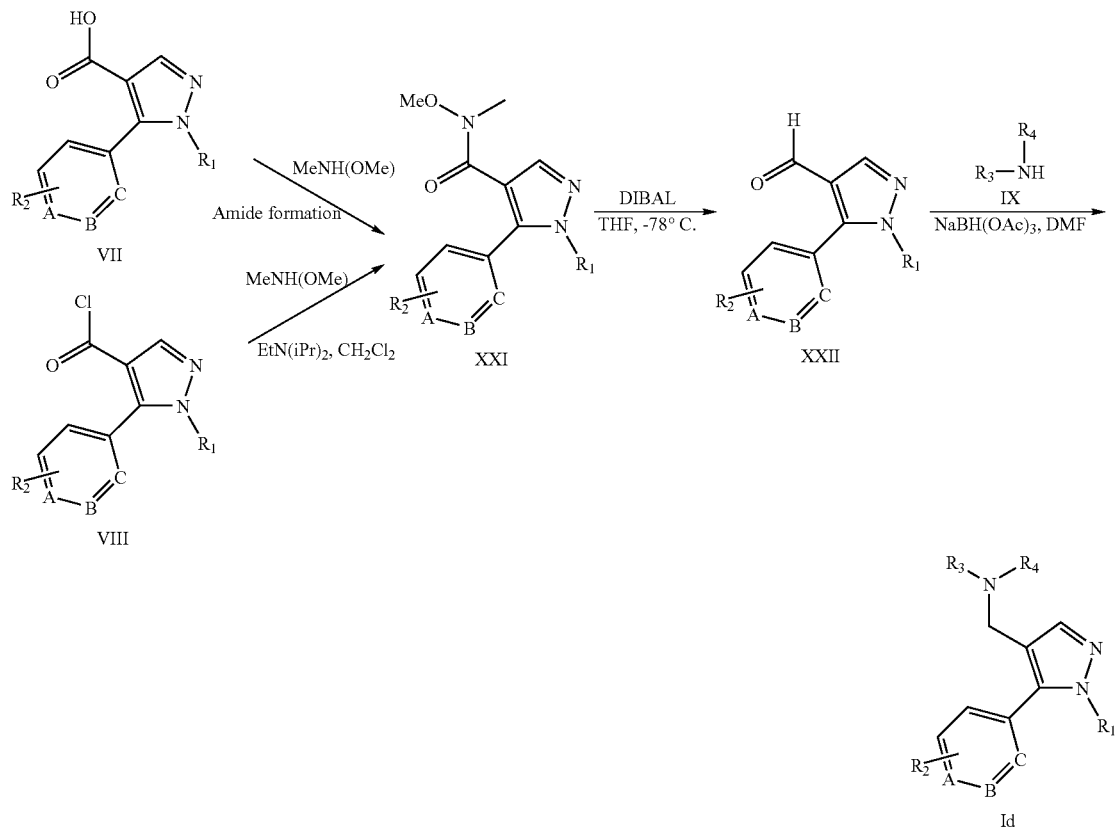

As illustrated in Scheme 5, compounds of formula Id were prepared from intermediates of formula VII, which were prepared as outlined in Scheme 1. Treatment of VII with N,O-dimethylhydroxylamine and an amide-bond forming reagent (e.g. diisopropylcarbodiimide) provides intermediates of formula XXI. Alternatively, treatment of intermediates of formula VIII (also prepared via Scheme 1) with a base and N,O-dimethylhydroxylamine affords intermediates of formula XXI. Treatment of intermediates of formula XXI with diisobutylaluminum hydride (DIBAL) affords intermediates of formula XXII. Treatment of XXII with intermediates of formula IX and sodium triacetoxyborohydride provides compounds of formula Id. Intermediates of formula IX can be obtained commercially, can be prepared by methods known in the literature, or can be readily prepared by one skilled in the art.

SCHEME 6

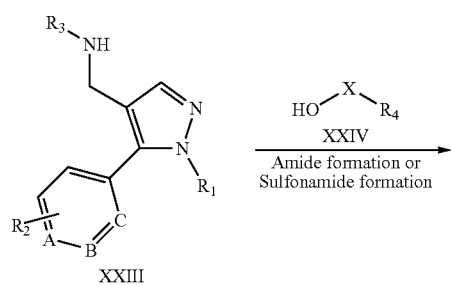

-continued

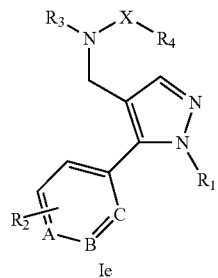

X = CO, SO$_2$

As illustrated in Scheme 6, compounds of formula Ie were prepared from intermediates of formula XXIII, which were prepared as outlined in Scheme 5 where intermediates IX are primary amines (R$_3$NH$_2$). Treatment of XXIII with intermediates of formula XXIV and an amide or sulfonamide bond forming reagent (e.g. diisopropylcarbodiimide) provides compounds of formula Ie. Alternatively, intermediates of formula XXIV were converted into their corresponding acyl or sulfonacyl chlorides and reacted with intermediates of formula XXIII in the presence of a base to afford compounds of formula Ie. Intermediates of formula XXIV can be obtained commercially, can be prepared by methods known in the literature, or can be readily prepared by one skilled in the art.

SCHEME 7

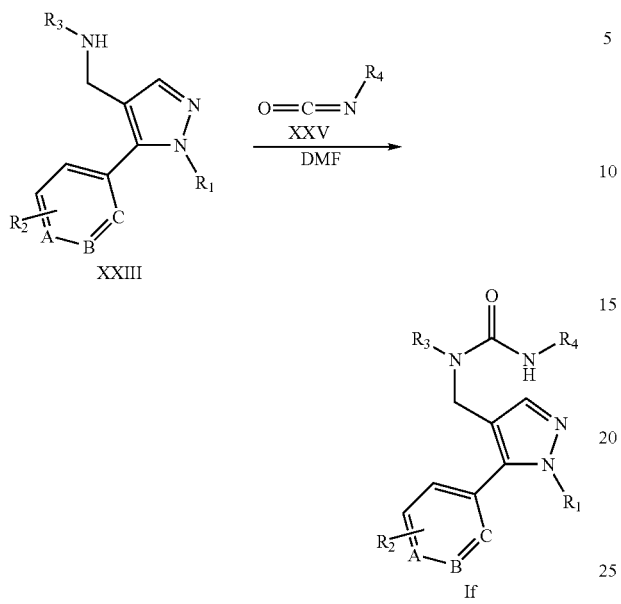

As illustrated in Scheme 7, compounds of formula If were prepared from intermediates of formula XXIII, which were prepared as outlined in Scheme 5 where intermediates IX are primary amines ($R_3NH_2$). Treatment of XXIII with intermediates of formula XXV provides compounds of formula If. Intermediates of formula XXV can be obtained commercially, can be prepared by methods known in the literature, or can be readily prepared by one skilled in the art.

SCHEME 8

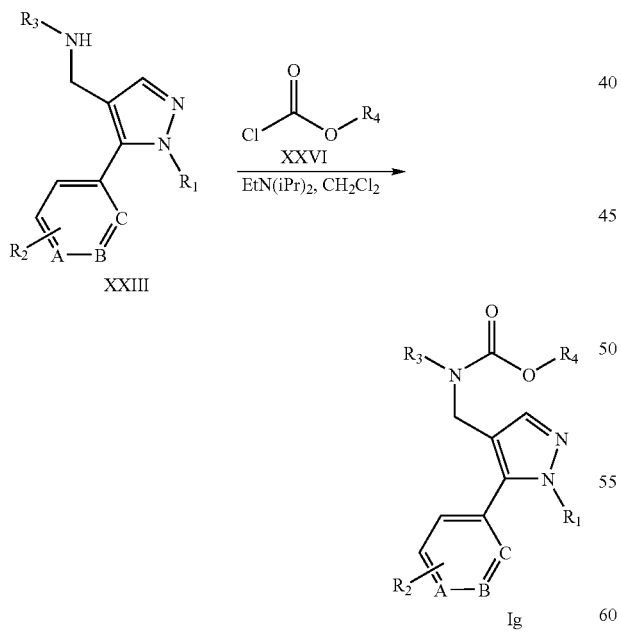

As illustrated in Scheme 8, compounds of formula Ig were prepared from intermediates of formula XXIII, which were prepared as outlined in Scheme 5 where intermediates IX are primary amines ($R_3NH_2$). Treatment of XXIII with intermediates of formula XXVI in the presence of a base provides compounds of formula Ig. Intermediates of formula XXVI can be obtained commercially, can be prepared by methods known in the literature, or can be readily prepared by one skilled in the art.

SCHEME 9

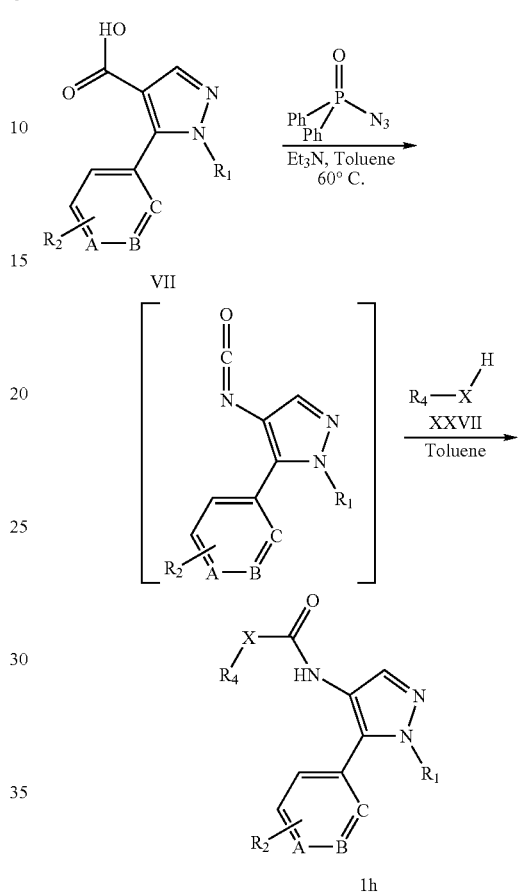

X = O, $NR_6$

As illustrated in Scheme 9, compounds of formula Ih were prepared from intermediates of formula VII, which were prepared as outlined in Scheme 1. Treatment of VII with diphenylphosphoryl azide in the presence of a base produces an intermediate isocyanate via the Curtius rearrangement. The isocyanate intermediate is not isolated but is treated with intermediates of formula XXVII to provide compounds of formula Ih. Intermediates of formula XXVII can be obtained commercially, can be prepared by methods known in the literature, or can be readily prepared by one skilled in the art.

SCHEME 10

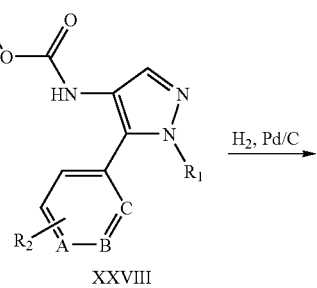

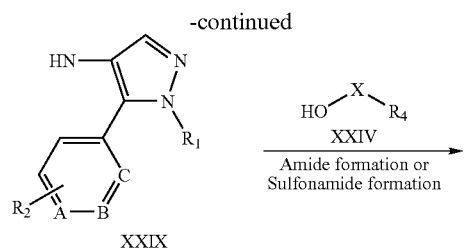

X = CO, SO₂

As illustrated in Scheme 10, compounds of formula Ii were prepared from intermediates of formula XXVIII, which were prepared as outlined in Scheme 9, where intermediate XXVII is benzyl alcohol. Treatment of XXVIII with hydrogen gas in the presence of a palladium catalyst (e.g. palladium on charcoal) removes the amine protecting group to provide intermediates of formula XXIX. Treatment of XXIX with intermediates of formula XXIV and an amide or sulfonamide bond forming reagent (e.g. diisopropylcarbodiimide) provides compounds of formula Ii. Alternatively, intermediates of formula XXIV were converted into their corresponding acyl or sulfonacyl chlorides and reacted with intermediates of formula XXIX in the presence of a base to afford compounds of formula Ii. Intermediates of formula XXIV can be obtained commercially, can be prepared by methods known in the literature, or can be readily prepared by one skilled in the art.

SCHEME 11

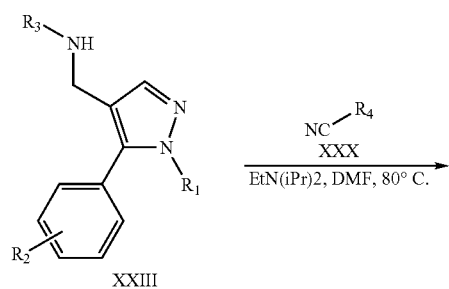

Compounds of formula Ij may be prepared as outlined in Scheme 11. Treatment of intermediates of formula XXIII with intermediates of formula XXX and a base provides compounds of formula UI. Intermediates of formula XXIII are prepared as outlined in Scheme 5 where intermediates DC are primary amines ($R_3NH_2$). Intermediates of formula XXX can be obtained commercially, can be prepared by methods known in the literature, or can be readily prepared by one skilled in the art.

SCHEME 12

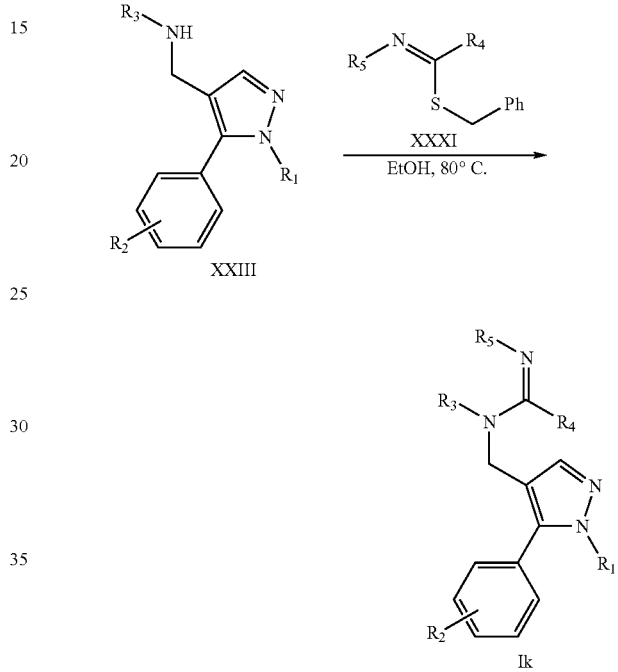

Compounds of formula Ik may be prepared as outlined in Scheme 12. Treatment of intermediates of formula XXIII with intermediates of formula XXXI provides compounds of formula Ik. Intermediates of formula XXIII are prepared as outlined in Scheme 5 where intermediates IX are primary amines ($R_3NH_2$). Intermediates of formula XXXI can be obtained commercially, can be prepared by methods known in the literature, or can be readily prepared by one skilled in the art.

SCHEME 13

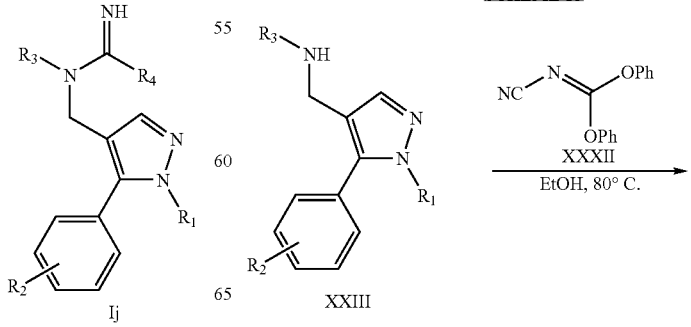

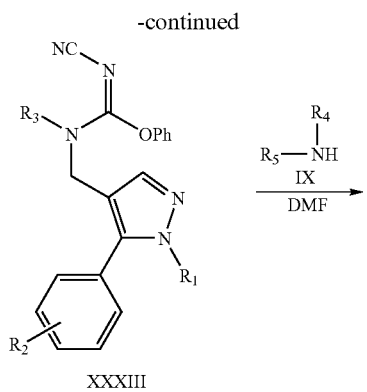

XXXIII

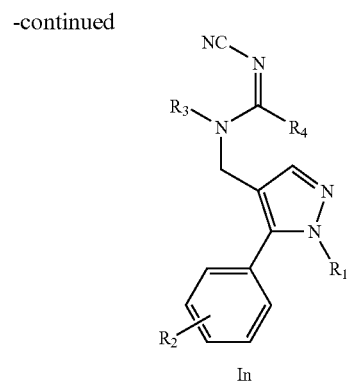

In

Compounds of formula In may be prepared as outlined in Scheme 14. Treatment of intermediates of formula XXIII with intermediates of formula XXXIV provides compounds of formula In. Intermediates of formula XXIII are prepared as outlined in Scheme 5 where intermediates IX are primary amines ($R_3NH_2$). Intermediates of formula XXXIV can be obtained commercially, can be prepared by methods known in the literature, or can be readily prepared by one skilled in the art.

SCHEME 15

Im

Compounds of formula Im may be prepared as outlined in Scheme 13. Treatment of intermediates of formula XXIII with intermediates of formula XXXII provides intermediates of formula XXXIII. Treatment of intermediates of formula XXXIII with intermediates of formula IX provides compounds of formula Im. Intermediates of formula XXIII are prepared as outlined in Scheme 5 where intermediates IX are primary amines ($R_3NH_2$). Intermediates of formula XXXII can be obtained commercially, can be prepared by methods known in the literature, or can be readily prepared by one skilled in the art. Intermediates of formula IX can be obtained commercially, can be prepared by methods known in the literature, or can be readily prepared by one skilled in the art.

SCHEME 14

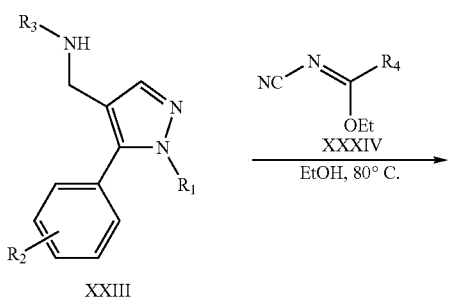

XXIII

Io

Compounds of formula Io may be prepared as outlined in Scheme 12. Treatment of intermediates of formula XXIII with intermediates of formula XXXV provides compounds of formula Io. Intermediates of formula XXIII are prepared as outlined in Scheme 5 where intermediates IX are primary amines ($R_3NH_2$). Intermediates of formula XXXV can be obtained commercially, can be prepared by methods known in the literature, or can be readily prepared by one skilled in the art.

SCHEME 16

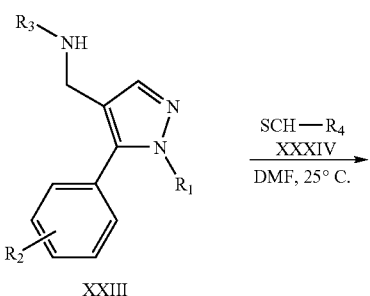

XXIII

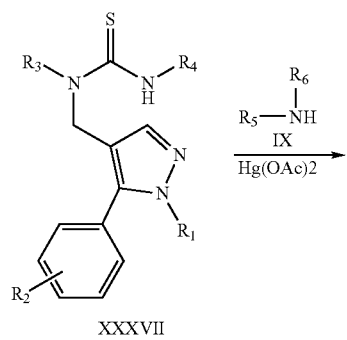

XXXVII

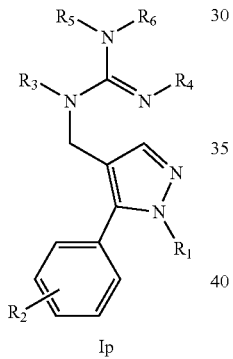

Ip

Compounds of formula Ip may be prepared as outlined in Scheme 16. Treatment of intermediates of formula XXIII with intermediates of formula XXXVI provides intermediates of formula XXXVII. Treatment of intermediates of formula XXXVII with intermediates of formula IX in the presence of a mercury(W) source (e.g. mercuric acetate) provides compounds of formula Ip. Intermediates of formula XXIII are prepared as outlined in Scheme 5 where intermediates IX are primary amines ($R_3NH_2$). Intermediates of formula XXXVI can be obtained commercially, can be prepared by methods known in the literature, or can be readily prepared by one skilled in the art. Intermediates of formula IX can be obtained commercially, can be prepared by methods known in the literature, or can be readily prepared by one skilled in the art.

EXAMPLES

The following examples serve to better illustrate, but not limit, some of the preferred embodiments of the invention.

Example 1

5-Biphenyl-4-yl-1-(7-chloro-quinolin-4-yl)-1H-pyrazole-4-carboxylic acid butyl-ethyl-amide

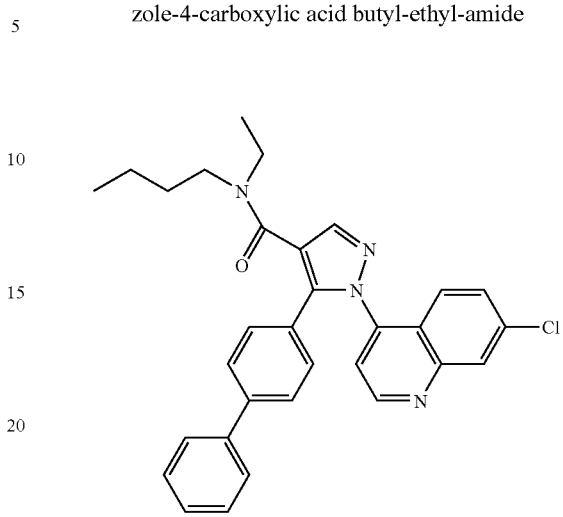

1A. t-butyl-4-biphenyl-β-keto ester

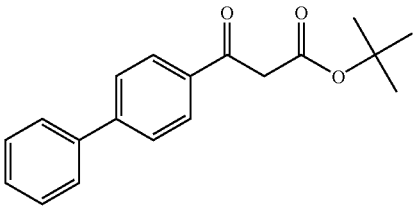

A mixture of methyl 4-biphenyl carboxylate (21.2 g 100 mmol) and t-butylacetate (26.1 g, 225 mmol) in THF (250 mL) was cooled to −78° C. under nitrogen. To the cooled solution was added dropwise 1M LiHMDS (225 mL, 225 mmol) over 1 h. The reaction was stirred at −78° C. for an additional 2 h and treated with aqueous 6N hydrochloric acid (200 mL), allowed to warm to 0° C. and extracted with ether (3×100 mL). The extracts are combined and washed successively with 1N hydrochloric acid (1×100 mL), water (1×100 mL), 10% aqueous sodium bicarbonate (2×100 mL) and saturated sodium chloride solution (1×100 mL). The organic extract was dried (anhydrous $MgSO_4$) and solvent removed in vacuo to afford the title compound (26 g, 80% yield), which was used in the next step without further purification.

M+1 (297.07), HPLC retention time (2.22 min). Analytical HPLC conditions: (Xterra Ms C18 S7 3.0×5.0 mm column, MeOH-Water gradient with 0.1% TFA).

$^1$H NMR $CH_3OD$: δ 8.04-8.06 (d, 2H), 7.767-7.783 (d, 2H), 7.684-7.699(d, 2H) 7.430-7.471 (m, 3H), 4.007 (S, 2H), 1.469 (S, 9H).

1B. t-butyl-4-biphenyl-β-keto ester vinylogous amide

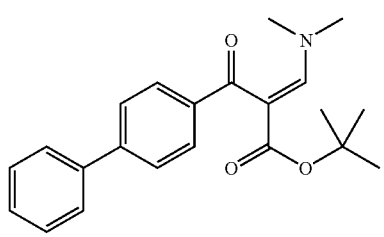

A mixture of compound 1A (14.8 g, 50 mmol) and N,N-dimethylformamide dimethyl acetal (20 mL, 150 mmol) in dichloroethane (50 mL) was heated at 70° C. for 6 h. Solvent was evaporated and the product was purified using silica gel column chromatography. 1% methanol in dichloroethane was used as eluent to yield (14 g, 80%) of the title compound.

M+1 (352.13), HPLC retention time (1.817 min)

$^1$H NMR CH$_3$OD: δ 7.789-7.805 (d, 2H), 7.677-7.730 (m, 4H), 7.466-7.497(t, 2H) 7.397-7.412 (m, 1H), 3.332 (Brs, 6H),1.215 (s, 9H).

$^{13}$CNMR (CDCl3): δ 195, 169.0, 156.7, 140.7, 140.4, 129.5, 129.0, 128.1, 127.1, 126.6, 80.0, 27.2.

1C. 5-(4-biphenyl)-1(7-chloro-4-hydrazinoquinolino)-1H-pyrazole-3-carboxylic acid-t-butyl ester

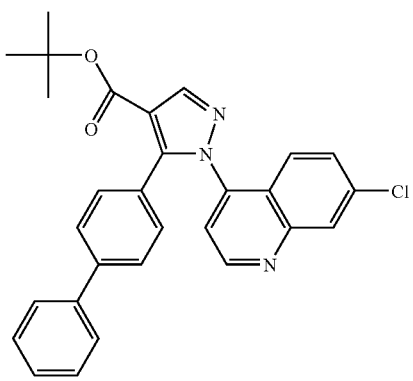

A mixture of compound 1B (500 mg, 1.42 mmol) and 7-chloro-4-hydrazinoquinoline (290 mg, 1.5 mmol) in anhydrous methanol (10 mL) were refluxed overnight. The reaction mixture was washed successively with 1N aqueous hydrochloric acid (5 mL), water (1×5 mL), 10% aqueous sodium bicarbonate (2×5 mL) and saturated sodium chloride solution (1×10 mL). The organic extract was dried (anhydrous MgSO4) and solvent removed in vacuo to yield the title compound (660 mg, 96% yield), which was used in the next step without further purification. M+1 (482.07), HPLC retention time (2.097 min)

1D. 5-(4-biphenyl)-1(7-chloro-4-hydrazinoquinolino)-1H-pyrazole-3-carboxylic acid

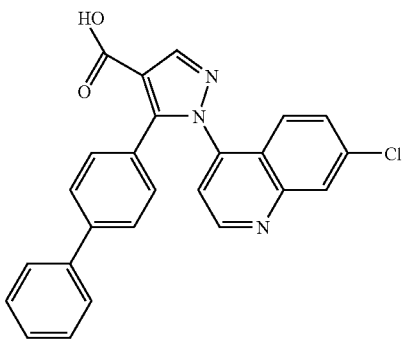

Compound 1C (500 mg, 1.03 mmol) was dissolved in 50% TFA in DCM (10 mL) and stirred at room temperature for 2 h. Solvent was removed in vacuo to give the corresponding acid (435 mg, 98% yield) that was used in the next step without purification. M+1 (426.21), HPLC retention time (1.810 min)

$^1$H NMR CDCl3: 8.846-8.856 (d, 1H), 8.378 (S,1H), 8.156-8.160 (d, 1H), 7.864(m, 2H),7.582 (s, 2H 7.478-7.582 (m, 4H),7.380-7.395 (m, 1H), 7.306-7.323 (m, 2H), 7.245-7.254 (d, 1H).

1E. 5-(4-biphenyl)-1(7-chloro-4-hydrazinoquinolino)-1H-pyrazole-3-carboxylic acid chloride

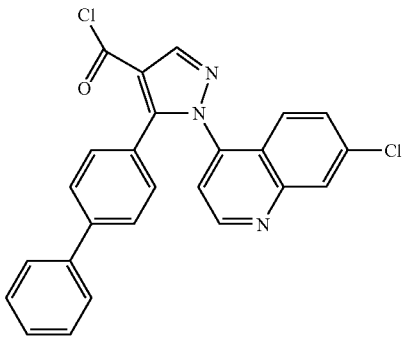

A mixture of compound 1D (100 mg, 0.2 mmol), oxalyl chloride (50.8 mg, 35 µl, 0.4 mmol) and a drop of dimethylformamide in dichloroethane (2 mL) was heated at reflux for 1 hour. Solvent was removed under vacuo and dried to give the title compound (100 mg, 96% yield) as a solid which was used in the next step without further purification.

1F. 5-Biphenyl-4-yl-1-(7-chloro-quinolin-4-yl)-1H-pyrazole-4-carboxylic acid butyl-ethyl-amide To a mixture of PS-DIEA (25 mg) in dichloroethane (500 µL) was added compound 1E (10 mg, 22 µmol) in DCE (250 µL) followed by N-ethyl-N-butyl amine (4.4 mg, 44 µmol) in DCE (250 µL). Contents were stirred overnight. Reaction mixture was filtered, the solvent was removed in vacuo and prep HPLC purification of the crude reaction mixture gave the title compound as a pure product (3 mg, 27%). Observed mass (510.16), HPLC retention time (1.983 min)

$^1$H NMR CDCl3: δ 8.893 (S, 1H),8.246 (S,1H), 7.981(m, 2H), 7.176-7.577 (m, 4H), 3.443-3.521 (m. 2H),3.066-3.220 (m, 2H), 0.749-1.560 (m, 10H).

Example 2

5-biphenyl-4-yl-1-(3-chloro-phenyl)-1H-pyrazole-4-carboxylic acid butylarnide

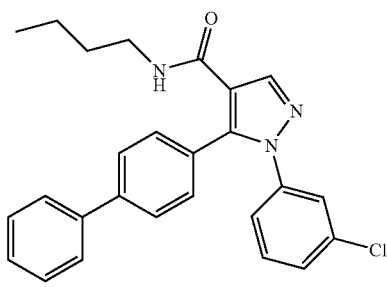

2A. butylarnine-derivatized polystyrene resin

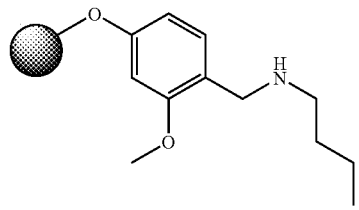

PL-FMP resin or similar aldehyde derivatized resin (~40 mg, 0.048 mmol) in a Microkan was suspended in a 7:3:1 mixture of anhydrous DMF-anhydrous trimethylorthoformate-acetic acid (2 mL). To this mixture was added n-butylamine, (5.2 mg, 0.72 mmol) followed by sodium triacetoxy borohydride (152 mg, 0.72 mmol). The resulting mixture was agitated for 72 h at room temperature using a shaker. Solvent was filtered, washed successively with (DMF, THF and DCM, 3×2 mL each), microkan containing the title compound was dried and used as is in the next step.

2B. 3-biphenyl-4-yl-N-butyl-3-oxo-propionamide derivatived polystyrene resin

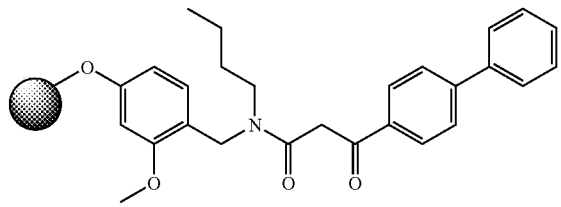

A single Microkan containing compound 2A was suspended in anhydrous N-methyl-2-pyrrolidinone (NMP) (1.5 mL) and to this was added, t-butyl-4-biphenyl-P-keto ester 2 (71 mg, 0.24 mmol), DMAP (0.1%). The resulting mixture in a sealed container was agitated for 48 h at 80° C. using a turbocoil shaker. Solvent was filtered and the microkan washed successively (DMF, THF and DCM, 3×2 mL each). The Microkan containing the title compound was dried and used in the next step.

2C. 2-(biphenyl-4-carbonyl)-N-butyl-3-dimethylamino-acrylamide derivatized polystyrene resin

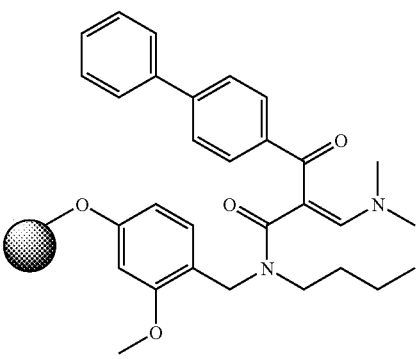

A single Microkan containing compound 2B was suspended in anhydrous DMF (1.0 mL) and to this was added dimethylformamide dimethyl acetal (DMF-DMA) (1 mL). The resultant mixture was heated with agitation in a sealed container at 70-80° C. for 24 h using a heating shaker. Solvent was filtered, and to the microkan was added DMF (1 mL) followed by DMF-DMA (1 mL) for the double treatment reaction. The resultant mixture was heated with agitation in a sealed container at 70-80° C. for 24 h using a turbocoil shaker. Solvent was filtered and the microkan containing the title compound was washed successively with DMF, THF and DCM (3×2 mL each) and dried.

2D. 5-biphenyl-4-yl-1-(3-chloro-phenyl)-1H-pyrazole-4-carboxylic acid butylarnide derivatized polystyrene resin

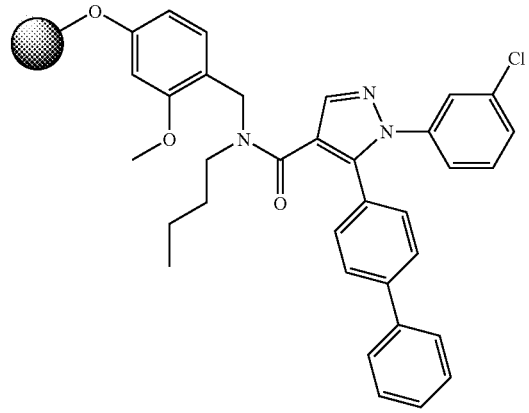

A single Microkan containing compound 2C was suspended in anhydrous N-methyl-2-pyrrolidinone (NMP) (1.5 mL) and to this was added, 3-chlorophenyl hydrazine (138 mg, 0.72 mmol) The resulting mixture in a sealed container was agitated for 72 h at 90° C. using a heated shaker. Solvent was filtered and the microkan containing the title compound was washed successively (DMF/MeOH(1:1), THF and DCM, 3×2 ml each) and dried.

2E. 5-biphenyl-4-yl-1-(3-chloro-phenyl)-1H-pyrazole-4-carboxylic acid butylamide Microkan containing compound 2D was suspended in a 1:1 trifluoroacetic acid and dichloromethane mixture (1.5 mL) for 1 h to cleave product from the resin. Reaction mixture was evaporated in vacuo to give the title compound (0.024 mmol). M+1=430.13, HPLC retention time 1.97 min $^1$H NMR CDCl$_3$ δ 8.178 (S, 1H), 7.664-7.681 (d, 2H), 7.615-7.618(d, 2H) 7.449-7.465 (d, 2H), 7.359-7.398 (m, 4H), 7.249 (S, 2H), 7.168 (S, 1H), 7.023 (S, 1H), 5.409 (br s, 1H), 3.234-3.273 (t,2H), 1.290-1.348 (m,2H), 1.108-1.153 (m,2H), 0.782-0.812 (t,3H).

Examples 3 to 52

Examples 3 to 52 in Table 1 were prepared by analogy to Example 2.

TABLE 1

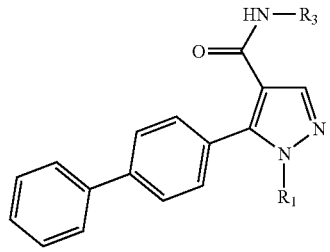

| Example | R$_3$ | R$_1$ | Observed Mass | HPLC RT (min) |
| --- | --- | --- | --- | --- |
| 3 | cyclohexylmethyl | 3-chlorophenyl | 470.32 | 2.18 |
| 4 | benzyl | 3-bromophenyl | 508.23 | 2.14 |
| 5 | 2-phenethyl | 3-bromophenyl | 522.03 | 2.20 |
| 6 | n-propyl | 7-chloro-guinolin-4-yl | 467.23 | 1.98 |
| 7 | 3-phenpropyl | 2-bromophenyl | 536.26 | 2.18 |
| 8 | 3-phenpropyl | 3-bromophenyl | 536.27 | 2.22 |
| 9 | 3-phenpropyl | 4-methoxyphenyl | 488.17 | 2.13 |
| 10 | 3-(methyl-phenyl-amino)-propyl | 3-bromophenyl | 565.06 | 1.89 |
| 11 | 3-(methyl-phenyl-amino)-propyl | 4-methoxyphenyl | 517.17 | 1.71 |
| 12 | 3-(methyl-phenyl-amino)-propyl | 2,5-difluorophenyl | 523.41 | 1.71 |
| 13 | cyclohexylmethyl | 3-bromophenyl | 514.17 | 2.20 |
| 14 | cyclohexylmethyl | 3-chloro-4-fluorophenyl | 488.34 | 2.30 |
| 15 | benzo[1,3]dioxol-5-yl-methyl | 1-naphthyl | 524.37 | 2.82 |
| 16 | 2-pyridin-2-yl-ethyl | 7-chloro-guinolin-4-yl | 530.37 | 1.64 |
| 17 | benzyl | 3-chlorophenyl | 464.36 | 2.06 |
| 18 | benzyl | 1-naphthyl | 480.22 | 2.97 |
| 19 | ethyl | 2,3-dimethylphenyl | 396.48 | 1.87 |
| 20 | 2-phenethyl | 2,3-dimethylphenyl | 472.46 | 2.93 |
| 21 | 3-phenpropyl | 7-chloro-guinolin-4-yl | 541.06 | 1.51 |
| 22 | 3-phenpropyl | 3-chlorophenyl | 492.12 | 2.16 |
| 23 | 3-phenpropyl | 2,3-dichlorophenyl | 526.27 | 1.23 |
| 24 | 3-phenpropyl | 3,5-dimethylphenyl | 486.25 | 2.99 |
| 25 | 3-phenpropyl | 2-trifluoromethylphenyl | 526.15 | 1.53 |
| 26 | 3-phenpropyl | 2,3-dimethylphenyl | 486.2 | 2.02 |
| 27 | n-butyl | 3-bromophenyl | 474.07 | 2.05 |
| 28 | cyclopropylmethyl | 3-bromophenyl | 472.03 | 1.45 |
| 29 | cyclopropylmethyl | 3-chloro-4-fluorophenyl | 446.35 | 2.10 |
| 30 | 2-phenoxyethyl | 3-bromophenyl | 538.17 | 2.20 |
| 31 | 3-(methyl-phenyl-amino)-propyl | 3-chlorophenyl | 521.24 | 1.82 |
| 32 | 3-(methyl-phenyl-amino)-propyl | 1-naphthyl | 537.47 | 1.74 |
| 33 | cyclohexylmethyl | 7-chloro-guinolin-4-yl | 519.12 | 2.19 |
| 34 | tetrahydrofuran-2-yl-methyl | 3-bromophenyl | 502.08 | 1.96 |
| 35 | pyridin-3-yl-methyl | 3-bromophenyl | 509.05 | 1.71 |
| 36 | benzyl | 7-chloro-guinolin-4-yl | 513.07 | 2.08 |
| 37 | n-propyl | 3-bromophenyl | 460.09 | 2.08 |
| 38 | 3-phenpropyl | 3-fluorophenyl | 476.17 | 2.07 |
| 39 | 3-phenpropyl | 2,5-difluorophenyl | 494.36 | 2.84 |
| 40 | 3-phenpropyl | 4-isopropylphenyl | 500.21 | 2.13 |
| 41 | 3-phenpropyl | 2,5-dichlorophenyl | 526.31 | 2.16 |
| 42 | 3-phenpropyl | 1-naphthyl | 508.40 | 2.04 |
| 43 | 3-phenpropyl | 2-ethylphenyl | 486.38 | 2.97 |
| 44 | 2-phenoxyethyl | 7-chloro-guinolin-4-yl | 545.37 | 2.95 |
| 45 | 2-phenoxyethyl | 3,5-dimethylphenyl | 488.45 | 3.02 |
| 46 | 3-(methyl-phenyl-amino)-propyl | 2-bromophenyl | 565.1 | 1.75 |
| 47 | 3-(methyl-phenyl-amino)-propyl | 3-methylphenyl | 501.22 | 1.76 |

TABLE 1-continued

| Example | R₃ | R₁ | Observed Mass | HPLC RT (min) |
|---|---|---|---|---|
| 48 | 3-(methyl-phenyl-amino)-propyl | 3-chloro-4-fluorophenyl | 537.09 | 1.83 |
| 49 | 3-(methyl-phenyl-amino)-propyl | 4-trifluoromethoxyphenyl | 571.37 | 0.97 |
| 50 | 3-(methyl-phenyl-amino)-propyl | 2,3-dimethylphenyl | 515.46 | 1.79 |
| 51 | 3-phenpropyl | 4-methanesulfonyl-phenyl | 536.28 | 1.92 |
| 52 | n-butyl | 1-naphthyl | 446.45 | 2.07 |

Examples 53 to 61

Examples 53 to 61 in Table 2 were prepared by analogy to Example 2.

TABLE 2

| Example | Structure | Observed Mass | HPLC RT (min) |
|---|---|---|---|
| 53 | 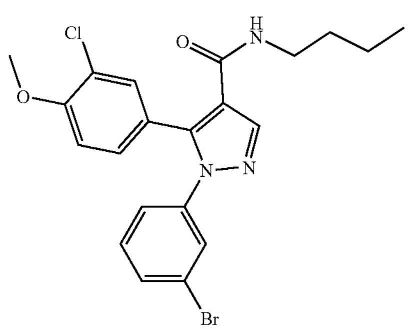 | 461.9 | 1.90 |
| 54 | 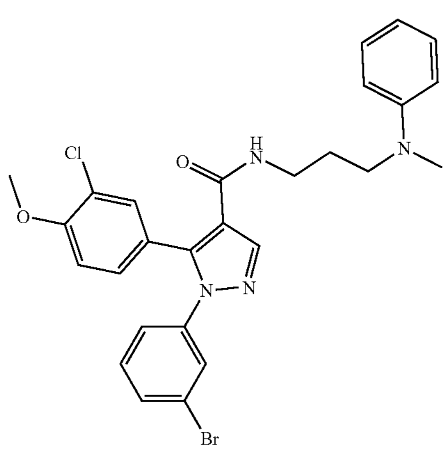 | 555.0 | 1.62 |

TABLE 2-continued

| Example | Structure | Observed Mass | HPLC RT (min) |
|---|---|---|---|
| 55 | 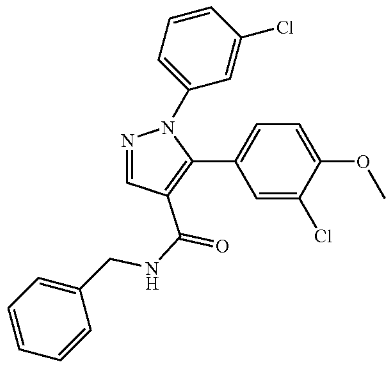 | 450.0 | 1.93 |
| 56 | 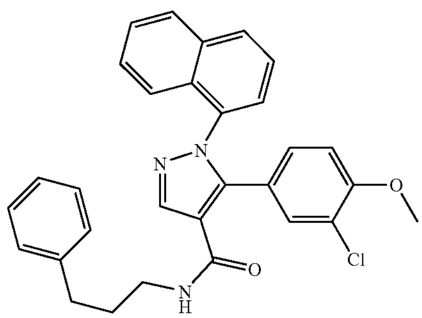 | 496.4 | 1.97 |
| 57 | 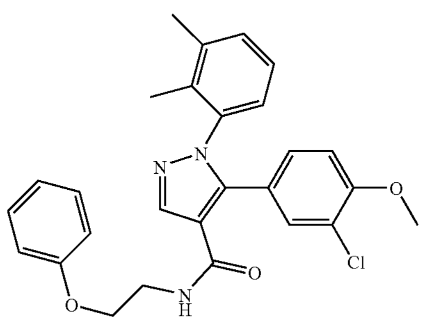 | 476.4 | 1.95 |
| 58 | 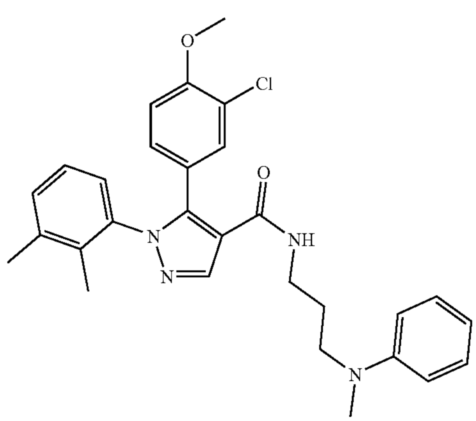 | 503.2 | 2.33 |

TABLE 2-continued

| Example | Structure | Observed Mass | HPLC RT (min) |
|---|---|---|---|
| 59 | 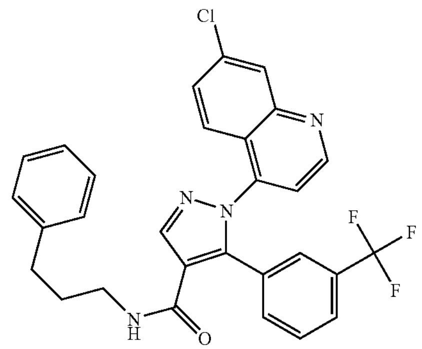 | 535.3 | 1.98 |
| 60 | 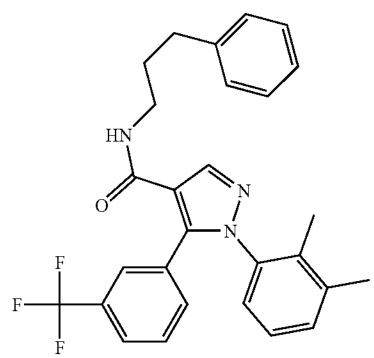 | 476.1 | 1.93 |
| 61 | 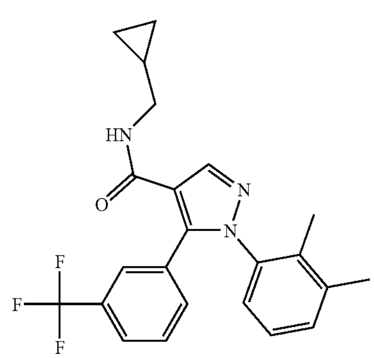 | 414.3 | 2.76 |

Examples 62 to 89

Examples 62 to 89 in Table 3 were prepared by analogy to Example 1.

TABLE 3

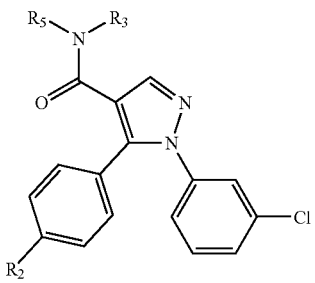

| Example | R$_2$ | R$_3$ | R$_4$ | Observed Mass | HPLC RT (min) |
|---|---|---|---|---|---|
| 62 | Ph | Benzyl | 2-dimethylaminoethyl | 535.5 | 1.21 |
| 63 | Cl | Phenyl | 2-pyridyl | 485.4 | 1.47 |
| 64 | Ph | benzyl | 2-pyridyl | 541.5 | 1.73 |
| 65 | Ph | ethyl | 3-tolylethylaminoethyl | 535.5 | 1.28 |
| 66 | Ph | methyl | benzyl | 478.4 | 1.67 |
| 67 | Cl | ethyl | benzyl | 450.4 | 1.70 |
| 68 | Cl | ethyl | n-butyl | 416.3 | 1.63 |
| 69 | Ph | n-propyl | cyclopropylmethyl | 470.4 | 1.83 |
| 70 | Cl | n-propyl | cyclopropylmethyl | 428.3 | 1.68 |
| 71 | Ph | cyclopropyl | H | 414.3 | 1.45 |
| 72 | Ph | cyclobutyl | H | 428.4 | 1.56 |
| 73 | Ph | 1-benzyl-piperidin-4-yl | H | 547.5 | 1.19 |
| 74 | Ph | 3-fluorophenyl | H | 468.4 | 1.79 |
| 75 | Cl | 3-fluorophenyl | H | 426.3 | 1.62 |
| 76 | Ph | 3-chlorophenyl | H | 484.4 | 1.86 |
| 77 | Cl | 3-chlorophenyl | H | 442.3 | 1.74 |
| 78 | Ph | 1-methyl-3-phenylpropyl | H | 506.5 | 1.80 |
| 79 | Cl | 1-methyl-3-phenylpropyl | H | 464.4 | 1.72 |
| 80 | Ph | 2-methylpropyl | H | 430.4 | 1.61 |
| 81 | Ph | 3-methylbutyl | H | 444.4 | 1.87 |
| 82 | Cl | 3-methylbutyl | H | 402.3 | 1.71 |
| 83 | Cl | 3-phenpropyl | H | 450.4 | 1.63 |
| 84 | Ph | 3-imidazol-1-yl-propyl | H | 482.4 | 1.15 |
| 85 | Ph | 1-benzyl-pyrrolidin-3-yl | H | 533.5 | 1.23 |
| 86 | Ph | 3-benzyloxy-1-ethyl-propyl | H | 536.5 | 1.82 |
| 87 | Cl | 3-benzyloxy-1-ethyl-propyl | H | 494.4 | 1.67 |
| 88 | Ph | methyl | methylbenzylaminoethyl | 535.5 | 1.25 |
| 89 | Cl | methyl | 2-phenethyl | 450.3 | 1.58 |

Examples 90 to 95

Examples 90 to 95 in Table 4 were prepared by analogy to Example 1.

TABLE 4

| Example | R$_2$ | G$_0$ | Observed Mass | HPLC RT (min) |
|---|---|---|---|---|
| 90 | Ph | 4-phenylpiperidyl | 518.5 | 1.82 |
| 91 | Cl | 4-phenylpiperidyl | 476.4 | 1.62 |
| 92 | Ph | 4-benzylpiperidyl | 532.5 | 1.90 |
| 93 | Cl | 4-benzylpiperidyl | 490.4 | 1.75 |
| 94 | Ph | 4-benzoylpiperidyl | 546.5 | 1.70 |
| 95 | Cl | 4-benzoylpiperidyl | 504.4 | 1.54 |

Examples 96 to 99

Examples 96 to 99 in Table 5 were prepared by analogy to Example 1.

TABLE 5

| Example | Structure | Observed Mass | HPLC RT (min) |
|---------|-----------|---------------|---------------|
| 96 | 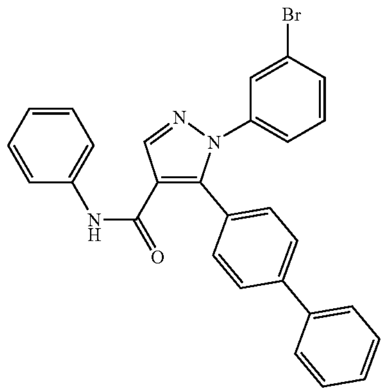 | 496 | 1.99 |
| 97 | 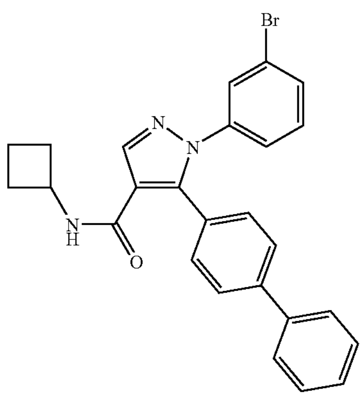 | 473 | 1.92 |
| 98 | 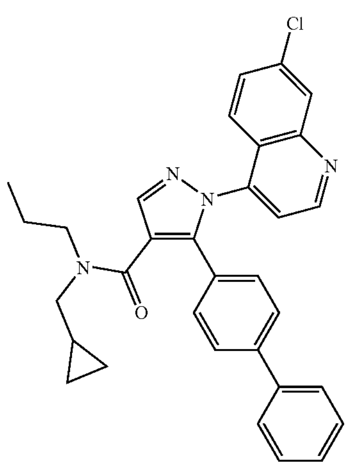 | 522 | 2.00 |

TABLE 5-continued

| Example | Structure | Observed Mass | HPLC RT (min) |
|---|---|---|---|
| 99 | 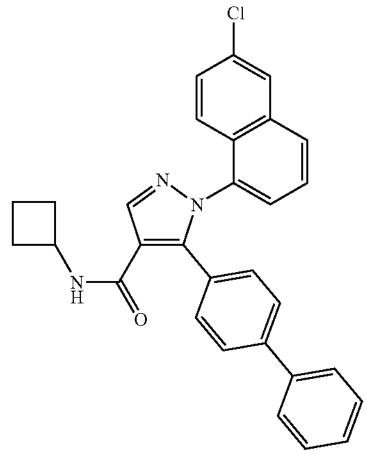 | 479 | 1.88 |

Examples 100 to 157

Examples 100 to 157 in Table 6 were prepared by analogy to Example 2.

TABLE 6

| Example | R₃ | R₁ | Observed Mass | HPLC RT (min) |
|---|---|---|---|---|
| 100 | benzo[1,3]dioxol-5-yl-methyl | 3-chlorophenyl | 508.2 | 2.07 |
| 101 | 2-methoxyethyl | 3,5-dichlorophenyl | 466.1 | 2.01 |
| 102 | 3-phenpropyl | 2-chlorophenyl | 492.4 | 2.09 |
| 103 | 3-phenpropyl | 2-methyl-4-chlorophenyl | 506.2 | 2.07 |
| 104 | 3-phenpropyl | 2,4-dimethylphenyl | 486.5 | 1.55 |
| 105 | 2-phenoxyethyl | 2-chlorophenyl | 494.3 | 2.06 |
| 106 | 2-phenoxyethyl | 3-chlorophenyl | 494.1 | 2.04 |
| 107 | 2-phenoxyethyl | 2,5-dimethylphenyl | 488.2 | 2.14 |
| 108 | 3-(methyl-phenyl-amino)-propyl | 2-methyl-4-chlorophenyl | 535.1 | 1.92 |
| 109 | benzo[1,3]dioxol-5-yl-methyl | 7-chloro-quinolin-4-yl | 557.0 | 2.04 |
| 110 | benzo[1,3]dioxol-5-yl-methyl | 2,3-dimethylphenyl | 502.4 | 2.93 |
| 111 | 2-pyridin-2-yl-ethyl | 1-napthyl | 495.3 | 1.12 |
| 112 | methyl | 4-trifluoromethoxyphenyl | 438.1 | 1.36 |
| 113 | 2-phenethyl | 3,4-dichlorophenyl | 512.0 | 2.27 |
| 114 | 3-phenpropyl | 2-methylphenyl | 472.5 | 2.07 |
| 115 | 3-phenpropyl | 3-methylphenyl | 472.2 | 2.16 |
| 116 | 3-phenpropyl | 3-chloro-4-methylphenyl | 506.2 | 2.14 |
| 117 | 3-phenpropyl | 3,5-dichlorophenyl | 526.3 | 2.36 |
| 118 | 3-phenpropyl | 3,4-dimethylphenyl | 486.2 | 2.20 |
| 119 | n-butyl | 3-chloro-4-fluorophenyl | 448.1 | 2.12 |
| 120 | n-butyl | 2,3-dimethylphenyl | 424.3 | 1.99 |
| 121 | cyclopropylmethyl | 3-fluorophenyl | 412.2. | 1.89 |
| 122 | cyclopropylmethyl | 2,3-dimethylphenyl | 422.2 | 1.90 |
| 123 | 2-phenoxyethyl | 3-methylphenyl | 474.1 | 1.99 |
| 124 | 2-phenoxyethyl | 3-fluorophenyl | 478.1 | 2.08 |
| 125 | 2-phenoxyethyl | 3-chloro-4-methylphenyl | 508.4 | 2.18 |
| 126 | 2-phenoxyethyl | 2-methyl-4-chlorophenyl | 508.1 | 2.19 |

TABLE 6-continued

| Example | R₃ | R₁ | Observed Mass | HPLC RT (min) |
|---|---|---|---|---|
| 127 | 2-phenoxyethyl | 2,4-dimethylphenyl | 488.4 | 2.09 |
| 128 | 2-phenoxyethyl | 2,5-difluorophenyl | 496.4 | 2.04 |
| 129 | 2-phenoxyethyl | 2-methoxyphenyl | 490.2 | 2.88 |
| 130 | 2-phenoxyethyl | 3-chloro-4-fluorophenyl | 512.2 | 2.12 |
| 131 | 2-phenoxyethyl | 2-methyl-5-fluorophenyl | 492.2 | 2.07 |
| 132 | 2-phenoxyethyl | 2-ethylphenyl | 488.2 | 2.15 |
| 133 | 3-(methyl-phenyl-amino)-propyl | 7-chloro-guinolin-4-yl | 572.4 | 2.42 |
| 134 | 3-(methyl-phenyl-amino)-propyl | 2-methylphenyl | 501.2 | 1.09 |
| 135 | 3-(methyl-phenyl-amino)-propyl | 2-ethylphenyl | 515.2 | 1.77 |
| 136 | 1-napthylmethyl | 7-chloro-guinolin-4-yl | 563.3 | 2.21 |
| 137 | benzo[1,3]dioxol-5-yl-methyl | 3-bromophenyl | 552.3 | 2.12 |
| 138 | 3-Morpholin-4-yl-propyl | 1-napthyl | 517.2 | 1.68 |
| 139 | benzyl | 2,3-dimethylphenyl | 458.4 | 2.81 |
| 140 | 2-methoxyethyl | 7-chloro-guinolin-4-yl | 481.1 | 1.89 |
| 141 | 2-phenethyl | 2,5-difluorophenyl | 480.4 | 2.76 |
| 142 | 3-phenpropyl | 4-methylphenyl | 472.2 | 2.09 |
| 143 | 3-phenpropyl | 2,5-dimethylphenyl | 486.5 | 2.17 |
| 144 | 3-phenpropyl | 3-chloro-4-fluorophenyl | 510.3 | 2.25 |
| 145 | 3-phenpropyl | 2-methyl-5-fluorophenyl | 490.2 | 1.97 |
| 146 | n-butyl | 2-methylphenyl | 410.2 | 1.94 |
| 147 | cyclopropylmethyl | 3-methylphenyl | 408.2 | 2.02 |
| 148 | cyclopropylmethyl | 3-chlorophenyl | 428.4 | 2.06 |
| 149 | cyclopropylmethyl | 3,4-dichlorophenyl | 462.1 | 2.18 |
| 150 | 2-phenoxyethyl | 3,4-dichlorophenyl | 528.0 | 2.24 |
| 151 | 2-phenoxyethyl | 3,4-dimethylphenyl | 488.4 | 1.18 |
| 152 | 2-phenoxyethyl | 2-trifluoromethylphenyl | 528.3 | 2.90 |
| 153 | 2-phenoxyethyl | 2,3-dimethylphenyl | 488.4 | 2.10 |
| 154 | 2-phenoxyethyl | 4-trifluoromethylphenyl | 528.4 | 2.21 |
| 155 | 3-(methyl-phenyl-amino)-propyl | 3-fluorophenyl | 505.2 | 1.74 |
| 156 | 3-(methyl-phenyl-amino)-propyl | 3,5-dichlorophenyl | 555.1 | 1.99 |
| 157 | 3-(methyl-phenyl-amino)-propyl | 2,3-dichlorophenyl | 555.1 | 1.93 |

Examples 158 to 171

Examples 158 to 171 in Table 7 were prepared by analogy to Example 2.

TABLE 7

| Example | R₁ | R₃ | G₁ | Observed Mass | HPLC RT (min) |
|---|---|---|---|---|---|
| 158 | 7-chloro-quinolin-4-yl | cyclohexylmethyl | 3,5-dimethoxyphenyl | 503.1 | 2.02 |
| 159 | 3-chloro-4-fluorophenyl | benzyl | 3-chloro-4-methoxyphenyl | 468.0 | 1.82 |
| 160 | 1-napthyl | benzyl | 3-chloro-4-methoxyphenyl | 466.0 | 1.74 |

TABLE 7-continued

| Example | $R_1$ | $R_3$ | $G_1$ | Observed Mass | HPLC RT (min) |
|---|---|---|---|---|---|
| 161 | 2-methyl-4-chlorophenyl | 3-phenpropyl | 3-trifluoromethylphenyl | 496.0 | 2.03 |
| 162 | 7-chloro-quinolin-4-yl | 2-phenoxyethyl | 3-chloro-4-methoxyphenyl | 533.3 | 1.96 |
| 163 | 2,5-difluorophenyl | 2-tetrahydrofuranylmethyl | 3-trifluoromethylphenyl | 450.1 | 1.73 |
| 164 | 2-methyl-4-chlorophenyl | benzo[1,3]dioxol-5-yl-methyl | 3,5-dimethoxyphenyl | 506.2 | 2.22 |
| 165 | 3,5-dichlorophenyl | benzyl | 3-chloro-4-methoxyphenyl | 485.9 | 2.07 |
| 166 | 2,5-dichlorophenyl | 2-phenoxyethyl | 3-chloro-4-methoxyphenyl | 516.0 | 1.83 |
| 167 | 2,5-dichlorophenyl | 2-phenoxyethyl | 3-trifluoromethylphenyl | 520.2 | 1.42 |
| 168 | 2-bromophenyl | 2-phenoxyethyl | 3,5-dimethoxyphenyl | 522.2 | 1.97 |
| 169 | 2-methyl-4-chlorophenyl | 3-phenpropyl | 4-dimethylaminophenyl | 473.2 | 1.90 |
| 170 | 1-napthyl | 3-phenpropyl | 3-chloro-4-methoxyphenyl | 496.4 | 1.97 |
| 171 | guinolinyl | 2-phenoxyethyl | 3-trifluoromethylphenyl | 535.0 | 1.89 |

Examples 172 to 236

Examples 172 to 236 in Table 8 were prepared by analogy to Example 1.

TABLE 8

| Example | $R_1$ | $R_3$ | Observed Mass | HPLC RT (min) |
|---|---|---|---|---|
| 172 | 2,4-dichlorophenyl | 1-benzyl-2-hydroxyethyl | 542.2 | 1.48 |
| 173 | 2,4-dichlorophenyl | 1-benzyloxymethyl-propyl | 570.4 | 1.97 |
| 174 | 3-chlorophenyl | 1-benzyl-pyrrolidin-3-yl | 533.5 | 1.23 |
| 175 | 3-chlorophenyl | 1-benzylsulfanylmethyl-2-hydroxyethyl | 554.3 | 1.55 |
| 176 | 2,4-dichlorophenyl | 1-hydroxycyclohexylmethyl | 520.2 | 1.60 |
| 177 | 3-chlorophenyl | 1-hydroxycyclohexylmethyl | 486.3 | 1.49 |
| 178 | 2,4-dichlorophenyl | 1-hydroxymethyl-2-methyl-butyl | 508.2 | 1.50 |
| 179 | 2,4-dichlorophenyl | 1-hydroxymethyl-2-methyl-propyl | 494.2 | 1.41 |
| 180 | 3-chlorophenyl | 1-hydroxymethyl-2-methyl-propyl | 460.2 | 1.37 |
| 181 | 2,4-dichlorophenyl | 1-hydroxymethyl-3-methylsulfanyl-propy | 526.2 | 1.40 |
| 182 | 3-chlorophenyl | 1-hydroxymethyl-3-methylsulfanyl-propy | 492.2 | 1.36 |
| 183 | 2,4-dichlorophenyl | 1-hydroxymethyl-propyl | 480.2 | 1.37 |
| 184 | 3-chlorophenyl | 1-hydroxymethyl-propyl | 446.2 | 1.38 |

TABLE 8-continued

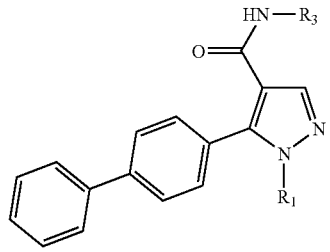

| Example | $R_1$ | $R_3$ | Observed Mass | HPLC RT (min) |
|---|---|---|---|---|
| 185 | 2,4-dichlorophenyl | 2-(2,6-dimethylphenoxy)-1-methyl-ethyl | 570.3 | 1.92 |
| 186 | 3-chlorophenyl | 2-(2,6-dimethylphenoxy)-1-methyl-ethyl | 536.1 | 1.94 |
| 187 | 3-chlorophenyl | 2-(2-hydroxyethylsulfanyl)-ethyl | 477.8 | 1.30 |
| 188 | 2,4-dichlorophenyl | 2-hydroxy-1,1-dimethyl-ethyl | 480.2 | 1.50 |
| 189 | 3-chlorophenyl | 2-hydroxy-1,1-dimethyl-ethyl | 446.2 | 1.40 |
| 190 | 2,4-dichlorophenyl | 2-hydroxy-1-methoxymethyl-2-phenethyl | 572.3 | 1.54 |
| 191 | 3-chlorophenyl | 2-hydroxy-1-methoxymethyl-2-phenethyl | 536.1 | 1.57 |
| 192 | 2,4-dichlorophenyl | 2-hydroxy-1-methyl-ethyl | 466.2 | 1.32 |
| 193 | 3-chlorophenyl | 2-hydroxy-1-methyl-ethyl | 432.2 | 1.28 |
| 194 | 2,4-dichlorophenyl | 2-hydroxy-2-phenethyl | 528.2 | 1.47 |
| 195 | 3-chlorophenyl | 2-hydroxy-2-phenyl-ethyl | 494.2 | 1.52 |
| 196 | 2,4-dichlorophenyl | 2-hydroxycyclohexyl | 506.2 | 1.45 |
| 197 | 3-chlorophenyl | 2-hydroxycyclohexyl | 472.2 | 1.41 |
| 198 | 2,4-dichlorophenyl | 2-hydroxyethyl | 452.2 | 1.24 |
| 199 | 3-chlorophenyl | 2-hydroxymethylphenyl | 480.2 | 1.49 |
| 200 | 2,4-dichlorophenyl | 2-hydroxypropyl | 466.4 | 1.35 |
| 201 | 3-chlorophenyl | 2-hydroxy-propyl | 431.9 | 1.26 |
| 202 | 2,4-dichlorophenyl | 2-methoxy-1-methyl-ethyl | 480.2 | 1.54 |
| 203 | 3-chlorophenyl | 2-methoxy-1-methyl-ethyl | 446.2 | 1.48 |
| 204 | 3-chlorophenyl | 2-phenoxy-1-piperidin-1-ylmethyl-ethyl | 591.5 | 1.79 |
| 205 | 2,4-dichlorophenyl | 2-phenoxyethyl | 526.1 | 1.79 |
| 206 | 2,4-dichlorophenyl | 3-(methyl-phenyl-amino)-propyl | 555.2 | 1.25 |
| 207 | benzyl | 3-(methyl-phenyl-amino)-propyl | 501.3 | 1.18 |
| 208 | 2,4-dichlorophenyl | 3-[bis-(2-hydroxyethyl)-amino]-propyl | 553.3 | 1.08 |
| 209 | 3-chlorophenyl | 3-chlorophenyl | 484.4 | 1.86 |
| 210 | 2,4-dichlorophenyl | 3-ethoxypropyl | 493.6 | 1.54 |
| 211 | 3-chlorophenyl | 3-ethoxypropyl | 460.2 | 1.46 |
| 212 | 2,4-dichlorophenyl | 3-hydroxybutyl | 466.2 | 1.25 |
| 213 | 3-chlorophenyl | 3-hydroxybutyl | 432.2 | 1.30 |
| 214 | 3-chlorophenyl | 3-hydroxyphenyl | 466.2 | 1.53 |
| 215 | 3-chlorophenyl | 3-methoxypropyl | 446.2 | 1.42 |
| 216 | 2,4-difluorophenyl | 3-phenpropyl | 494.3 | 1.66 |
| 217 | 3-chlorophenyl | 4-hydroxyethylphenyl | 494.6 | 1.43 |
| 218 | 3-chlorophenyl | 4-hydroxymethylphenyl | 480.2 | 1.41 |
| 219 | 2,4-dichlorophenyl | 4-hydroxypropyl | 480.2 | 1.33 |
| 220 | 3-chlorophenyl | 4-hydroxypropyl | 446.2 | 1.26 |
| 221 | 3-chlorophenyl | 4-phenoxyphenyl | 542.3 | 1.94 |
| 222 | 2,4-dichlorophenyl | 5-methylfuran-2-ylmethyl | 502.2 | 1.72 |
| 223 | 3-chlorophenyl | 5-methylfuran-2-ylmethyl | 468.2 | 1.68 |
| 224 | 3-chlorophenyl | 6-hydroxyhexyl | 460.2 | 1.29 |
| 225 | 3-chlorophenyl | 6-hydroxyhexyl | 472.2 | 1.32 |
| 226 | 2,4-dichlorophenyl | butyl | 464.2 | 1.66 |
| 227 | 2,4-difluorophenyl | butyl | 432.2 | 1.54 |
| 228 | 3-chlorophenyl | cyclobutyl | 428.4 | 1.56 |
| 229 | 2,4-dichlorophenyl | cyclopropylmethyl | 462.2 | 1.56 |
| 230 | 2,4-difluorophenyl | cyclopropylmethyl | 430.2 | 1.48 |
| 231 | 2,4-dichlorophenyl | furan-2-ylmethyl | 488.2 | 1.55 |
| 232 | 3-chlorophenyl | furan-2-ylmethyl | 454.2 | 1.60 |
| 233 | 2,4-dichlorophenyl | piperidin-1-yl | 491.2 | 1.52 |
| 234 | 3-chlorophenyl | piperidin-1-yl | 457.2 | 1.44 |
| 235 | 2,4-dichlorophenyl | tetrahydrofuran-2-ylmethyl | 492.2 | 1.48 |
| 236 | 3-chlorophenyl | tetrahydrofuran-2-ylmethyl | 458.2 | 1.47 |

Examples 237 to 280

Examples 237 to 280 in Table 9 were prepared by analogy to Example 2.

TABLE 9

| Example | R₁ | R₂ | R₃ | Observed Mass | HPLC RT (min) |
|---|---|---|---|---|---|
| 237 | 2,4-dichlorophenyl | 4-chloro | 3-phenpropyl | 484.1 | 1.66 |
| 238 | 2,4-difluorophenyl | 4-chloro | 3-phenpropyl | 452.2 | 1.53 |
| 239 | 3-chloro-4-fluorophenyl | 4-chloro | 3-phenpropyl | 468.2 | 1.63 |
| 240 | 2,3-dimethylphenyl | 4-chloro | 3-phenpropyl | 444.2 | 1.60 |
| 241 | 2,4-dichlorophenyl | 3-bromo | 3-phenpropyl | 530.1 | 1.68 |
| 242 | benzyl | 4-trifluoromethyl | 3-phenpropyl | 464.2 | 1.57 |
| 243 | 3-chlorophenyl | 4-trifluoromethyl | 3-phenpropyl | 484.2 | 1.73 |
| 244 | 2,4-difluorophenyl | 4-trifluoromethyl | 3-phenpropyl | 486.2 | 1.61 |
| 245 | 2-chloro-4-trifluoromethylphenyl | 4-trifluoromethyl | 3-phenpropyl | 552.2 | 1.74 |
| 246 | 6-chloro-4-trifluoromethylpyridin-2-yl | 4-trifluoromethyl | 3-phenpropyl | 553.2 | 1.69 |
| 247 | 2,3-dimethylphenyl | 4-trifluoromethyl | 3-phenpropyl | 478.2 | 1.61 |
| 248 | 4-trifluoromethyl-2-pyridyl | 4-trifluoromethyl | 3-phenpropyl | 519.2 | 1.68 |
| 249 | 2,4-dichlorophenyl | 4-cyano | 3-phenpropyl | 475.2 | 1.51 |
| 250 | 2,4-dichlorophenyl | 4-chloro | butyl | 422.1 | 1.54 |
| 251 | 2,4-difluorophenyl | 4-chloro | butyl | 390.2 | 1.38 |
| 252 | 2,4-dichlorophenyl | 4-trifluoromethyl | butyl | 456.1 | 1.61 |
| 253 | 3-chlorophenyl | 4-trifluoromethyl | butyl | 422.1 | 1.58 |
| 254 | 2,4-difluorophenyl | 4-trifluoromethyl | butyl | 424.2 | 1.42 |
| 255 | 3-chloro-4-fluorophenyl | 4-trifluoromethyl | butyl | 440.1 | 1.58 |
| 256 | 2-chloro-4-trifluoromethylphenyl | 4-trifluoromethyl | butyl | 490.1 | 1.60 |
| 257 | 6-chloro-4-trifluoromethyl-2-pyridyl | 4-trifluoromethyl | butyl | 491.2 | 1.51 |
| 258 | 4-chloro-6-trifluoromethyl-2-pyridyl | 4-trifluoromethyl | butyl | 491.1 | 1.52 |
| 259 | 2,6-dichloro-4-pyridyl | 4-trifluoromethyl | butyl | 457.1 | 1.39 |
| 260 | 2,4-dichlorophenyl | 4-chloro | cyclopropylmethyl | 420.1 | 1.49 |
| 261 | 2,4-dichlorophenyl | 4-bromo | cyclopropylmethyl | 466.1 | 1.52 |
| 262 | 2,4-difluorophenyl | 4-bromo | cyclopropylmethyl | 432.1 | 1.35 |
| 263 | 2,4-difluorophenyl | 4-trifluoromethyl | cyclopropylmethyl | 422.2 | 1.36 |
| 264 | 2,4-dichlorophenyl | 4-chloro | 3-(methyl-phenyl-amino)-propyl | 513.1 | 1.19 |
| 265 | 2,4-dichlorophenyl | 4-bromo | 3-(methyl-phenyl-amino)-propyl | 559.1 | 1.17 |
| 266 | 2,4-difluorophenyl | 4-trifluoromethyl | 3-(methyl-phenyl-amino)-propyl | 515.2 | 1.12 |
| 267 | 2-chloro-4-trifluoromethylphenyl | 4-trifluoromethyl | 3-(methyl-phenyl-amino)-propyl | 581.2 | 1.23 |
| 268 | 6-chloro-4-trifluoromethylpyridin-2-yl | 4-trifluoromethyl | 3-(methyl-phenyl-amino)-propyl | 582.2 | 1.17 |
| 269 | 2,4-dichlorophenyl | 4-cyano | 3-(methyl-phenyl-amino)-propyl | 504.2 | 1.08 |
| 270 | 2,4-difluorophenyl | 4-bromo | 3-phenpropyl | 496.1 | 1.57 |
| 271 | 3-chloro-4-fluorophenyl | 4-bromo | 3-phenpropyl | 514.1 | 1.69 |
| 272 | 2,4-difluorophenyl | 3-bromo | 3-phenpropyl | 496.2 | 1.51 |
| 273 | 2,4-difluorophenyl | 4-cyano | 3-phenpropyl | 443.2 | 1.39 |
| 274 | 3-chloro-4-fluorophenyl | 4-cyano | 3-phenpropyl | 459.2 | 1.46 |
| 275 | 3-chlorophenyl | 4-trifluoromethyl | cyclopropylmethyl | 420.1 | 1.46 |
| 276 | 2,3-dimethylphenyl | 4-trifluoromethyl | 3-(methyl-phenyl-amino)-propyl | 507.3 | 1.14 |

TABLE 9-continued

| Example | R₁ | R₂ | R₃ | Observed Mass | HPLC RT (min) |
|---|---|---|---|---|---|
| 277 | 2,4-difluorophenyl | 4-cyano | 3-(methyl-phenyl-amino)-propyl | 472.3 | 1.03 |
| 278 | 2,4-dichlorophenyl | 4-trifluoromethyl | cyclopropylmethyl | 454.1 | 1.54 |
| 279 | 2,4-dichlorophenyl | 4-trifluoromethyl | 3-(methyl-phenyl-amino)-propyl | 547.1 | 1.22 |
| 280 | 2,4-dichlorophenyl | 4-bromo | 3-phenpropyl | 530.0 | 1.82 |

Example 281

1-(2,4-Dichloro-phenyl)-5-(3-thiophen-2-yl-phenyl)-1H-pyrazole-4-carboxylic acid (1-benzyloxymethyl-propyl)-amide

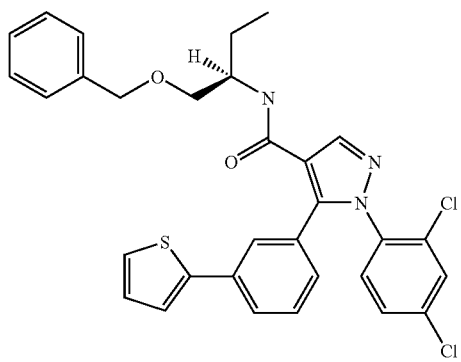

281A. 5-(3-Bromo-phenyl)-1-(2,4-dichloro-phenyl)-1H-pyrazole-4-carboxylic acid (1-benzyloxymethyl-propyl)-amide

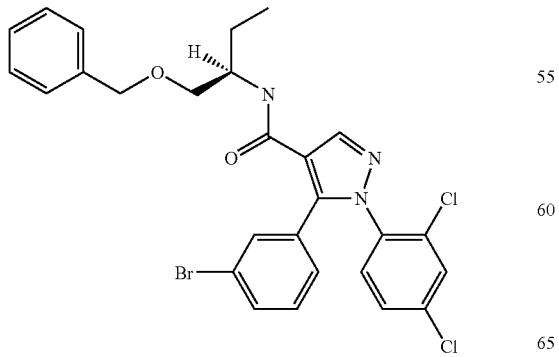

Compound 218A was prepared by analogy to Example 1.

281B. 1-(2,4-Dichloro-phenyl)-5-(3-thiophen-2-yl-phenyl)-1H-pyrazole-4-carboxylic acid (1-benzyloxymethyl-propyl)-amide To a solution of 281A (27 mg, 50 umol) in 1 mL dioxane was added 2M solution of $K_3PO_4$ (100 uL), $Pd(PPh_3)_4$ (3 mg, 2 umol) and the contents were degassed and purged with nitrogen. To this solution was added 3-thiophene boronic acid (7 mg, 55 umol) and the resulting mixture was heated in a sealed 1 dram vial at 110° C. for 48 h. Contents were cooled to room temperature and passed through a waters HLB u elution plate to get rid of insoluble material and the filtrate was further purified via prep HPLC (Xterra 10×50 mm, S5 column, MeOH—Water gradient) to give the title compound. HPLC retention time (2.04 min). Observed mass 576.13.

Examples 282 to 306

Examples 282 to 306 in Table 10 were prepared by analogy to Example 281.

TABLE 10

[Chemical structure: pyrazole with C(=O)NH-R3 at 4-position, R2-phenyl at 5-position, R1 at N1]

| Example | R₁ | R₂ | R₃ | Observed Mass | HPLC RT (min) |
|---|---|---|---|---|---|
| 282 | 2,4-dichlorophenyl | 2-benzothiophenyl | 1-benzyloxymethyl-propyl | 626.1 | 2.07 |
| 283 | 2,4-dichlorophenyl | 2-benzothiophenyl | butyl | 520.1 | 1.53 |
| 284 | 3-chlorophenyl | 2-chlorophenyl | butyl | 464.1 | 1.78 |
| 285 | 3-chlorophenyl | 2-furyl | 1-benzyloxymethyl-propyl | 526.1 | 1.72 |
| 286 | 2,4-dichlorophenyl | 2-furyl | 1-benzyloxymethyl-propyl | 560.1 | 2.45 |
| 287 | 3-chlorophenyl | 2-methoxyphenyl | butyl | 460.1 | 1.60 |
| 288 | 3-chlorophenyl | 2-thiophenyl | butyl | 436.1 | 1.63 |
| 289 | 2,4-dichlorophenyl | 3,5-dichlorophenyl | 1-benzyloxymethyl-propyl | 640.1 | 1.64 |
| 290 | 2,4-dichlorophenyl | 3-benzothiophenyl | 1-benzyloxymethyl-propyl | 626.1 | 2.12 |
| 291 | 3-chlorophenyl | 3-benzothiophenyl | butyl | 486.1 | 1.79 |
| 292 | 3-chlorophenyl | 4-hydroxymethylphenyl | 1-benzyloxymethyl-propyl | 566.1 | 1.46 |
| 293 | 2,4-dichlorophenyl | 4-methoxyphenyl | 1-benzyloxymethyl-propyl | 600.2 | 1.64 |
| 294 | 3-chlorophenyl | 4-methoxyphenyl | butyl | 460.1 | 1.56 |
| 295 | 2,4-dichlorophenyl | 4-methylsulfonylphenyl | 1-benzyloxymethyl-propyl | 648.1 | 1.84 |
| 296 | 2,4-dichlorophenyl | 4-methylsulfonylphenyl | butyl | 542.1 | 1.97 |
| 297 | 2,4-dichlorophenyl | 5-chloro-2-thiophenyl | 1-benzyloxymethyl-propyl | 612.1 | 1.11 |
| 298 | 3-chlorophenyl | 5-chloro-2-thiophenyl | butyl | 470.1 | 1.75 |
| 299 | 2,4-dichlorophenyl | phenyl | 1-benzyloxymethyl-propyl | 570.1 | 2.05 |
| 300 | 3-chlorophenyl | 5-acetyl-thiophen-2-yl | 1-benzyloxymethyl-propyl | 584.1 | 1.60 |
| 301 | 2,4-dichlorophenyl | 5-acetyl-thiophen-2-yl | 1-benzyloxymethyl-propyl | 618.2 | 1.72 |
| 302 | 2,4-dichlorophenyl | indol-5-yl | 1-benzyloxymethyl-propyl | 609.2 | 1.73 |
| 303 | 2,4-dichlorophenyl | isobutyl | 1-benzyloxymethyl-propyl | 550.2 | 1.87 |
| 304 | 3-chlorophenyl | isoxazole | 1-benzyloxymethyl-propyl | 555.0 | 1.59 |
| 305 | 3-chlorophenyl | n-butyl | 1-benzyloxymethyl-propyl | 516.2 | 2.04 |
| 306 | 2,4-dichlorophenyl | n-butyl | 1-benzyloxymethyl-propyl | 550.2 | 1.77 |

Examples 307 to 318

Examples 307 to 318 in Table 11 were prepared by analogy to Example 281.

TABLE 11

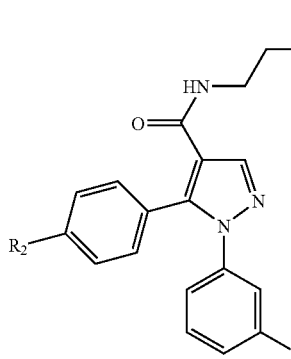

| Example | R₂ | Observed Mass | HPLC RT (min) |
|---|---|---|---|
| 307 | 2-chlorophenyl | 464.1 | 1.80 |
| 308 | 2-furyl | 420.5 | 1.48 |
| 309 | 2-methoxyphenyl | 460.2 | 1.62 |
| 310 | 2-methylphenyl | 444.2 | 1.77 |
| 311 | 2-thiophenyl | 436.4 | 1.59 |
| 312 | 3,5-dichlorophenyl | 498.1 | 2.01 |
| 313 | 3-pyridyl | 431.1 | 1.27 |

TABLE 11-continued

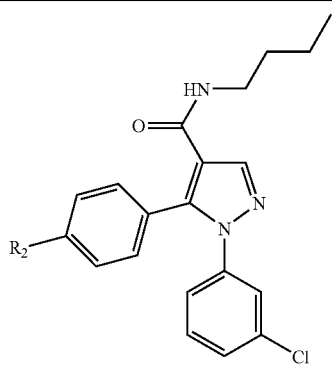

| Example | R₂ | Observed Mass | HPLC RT (min) |
|---|---|---|---|
| 314 | 4-hydroxymethylphenyl | 460.3 | 1.27 |
| 315 | 4-methoxyphenyl | 460.2 | 1.57 |
| 316 | 4-methylsulfonylphenyl | 508.2 | 1.31 |
| 317 | 4-pyridyl | 431.2 | 1.24 |
| 318 | quinolin-8-yl | 481.6 | 1.60 |

Examples 319 to 334

Examples 319 to 334 in Table 12 were prepared by analogy to Example 1.

TABLE 12

| Example | Structure | Observed Mass | HPLC RT (min) |
|---|---|---|---|
| 319 | 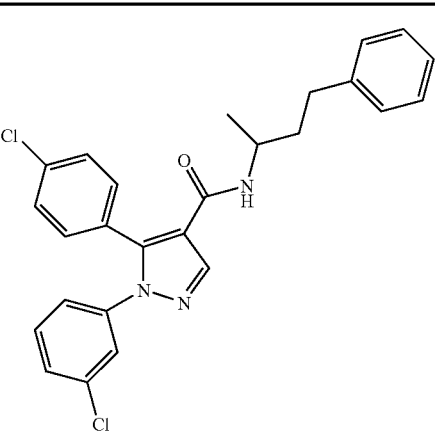 | 464.4 | 1.72 |
| 320 | 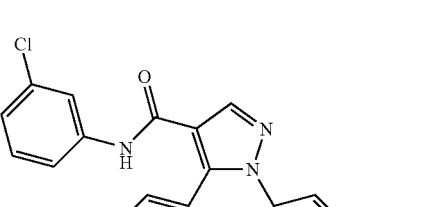 | 442.3 | 1.74 |

TABLE 12-continued

| Example | Structure | Observed Mass | HPLC RT (min) |
|---|---|---|---|
| 321 | 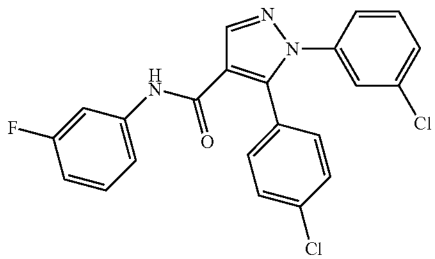 | 426.3 | 1.62 |
| 322 | 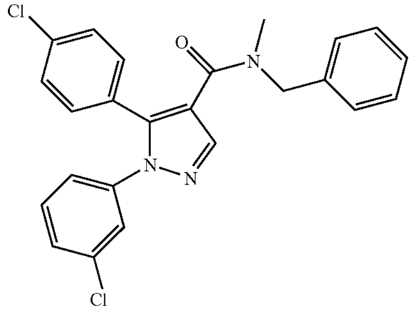 | 436.6 | 1.53 |
| 323 | 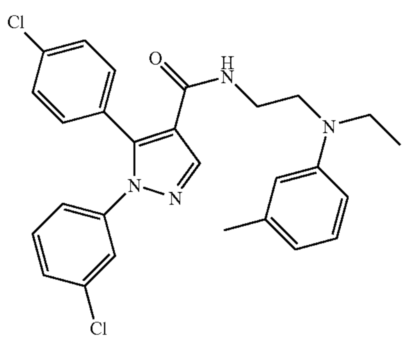 | 493.4 | 1.19 |
| 324 | Chiral | 494 | 1.67 |

TABLE 12-continued

| Example | Structure | Observed Mass | HPLC RT (min) |
|---|---|---|---|
| 325 | 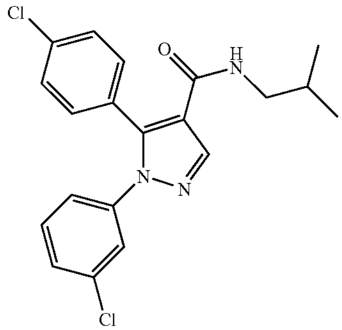 | 388.3 | 1.45 |
| 326 | 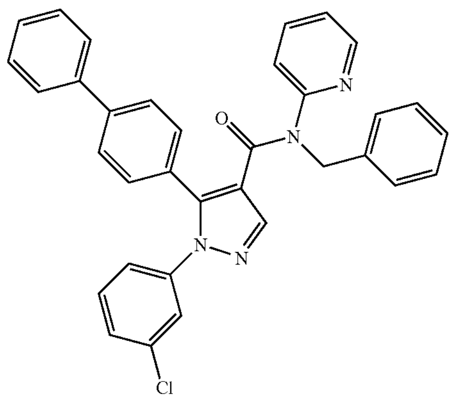 | 541.5 | 1.73 |
| 327 | 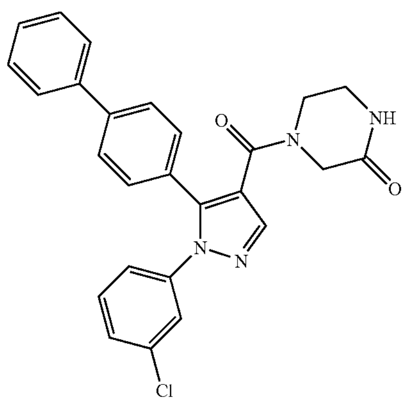 | 457.2 | 1.22 |
| 328 | 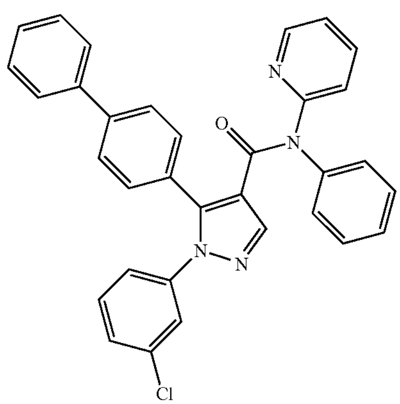 | 527.4 | 1.65 |

TABLE 12-continued

| Example | Structure | Observed Mass | HPLC RT (min) |
|---------|-----------|---------------|---------------|
| 329 | 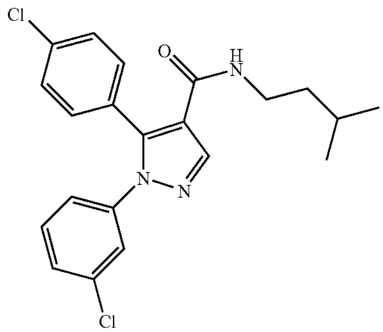 | 402.3 | 1.71 |
| 330 | 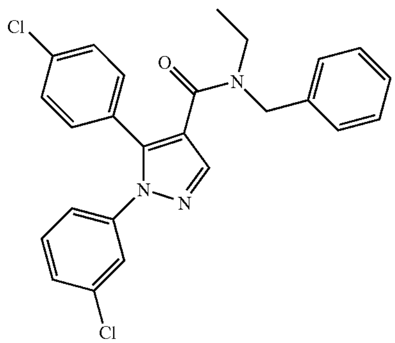 | 450.4 | 1.70 |
| 331 | 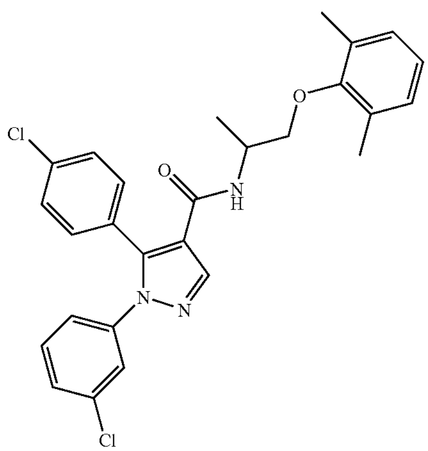 | 494.4 | 1.76 |
| 332 | 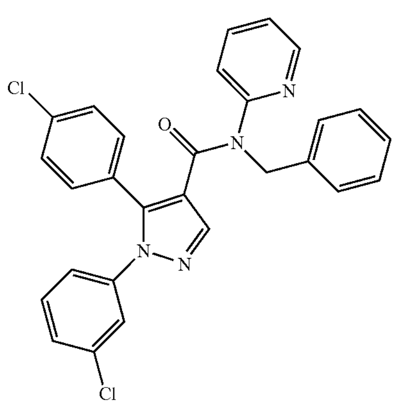 | 499.4 | 1.60 |

TABLE 12-continued

| Example | Structure | Observed Mass | HPLC RT (min) |
|---|---|---|---|
| 333 | 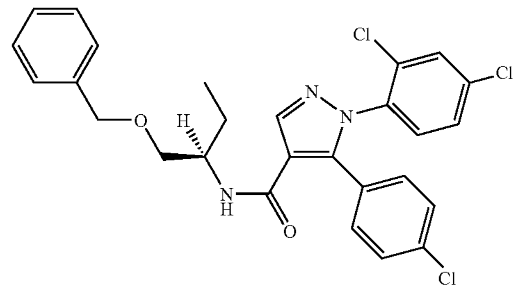 | 530.2 | 2.14 |
| 334 | 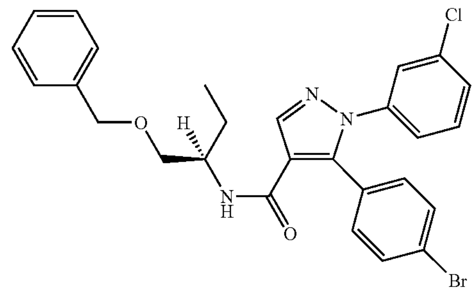 | 540.5 | 2.10 |

Biological Evaluation

Cannabinoid Receptor Binding Assay

Radioligand binding studies were conducted in membranes prepared from Chinese Hamster Ovary (CHO) cells that over-express recombinant human CB-1 (CHO-CB-1 cells). Total assay volume for the binding studies was 100 μl. 5 μg of membranes were brought up to a final volume of 95 μl with Binding Buffer (25 mM HEPES, 150 mM NaCl, 2.5 mM $CaCl_2$, 1 mM $MgCl_2$, 0.25% BSA). The diluted membranes were preincubated with a compound or DMSO vehicle. The binding reaction was initiated by the addition of 2 nM final $^3$H-CP-55,940 (120 Ci/mmol) and proceeded for 2.5 hours at room temperature. The binding reaction was terminated by transferring the reaction to GF/B 96 well plates (presoaked with 0.3% polyethylenimine) using a Packard Cell Harvester. The filter was washed with 0.25×PBS, 30 μl MicroScint was added per well, and the bound radiolabel was quantitated by scintillation counting on a Packard TopCount Scintillation Counter. The CB-2 radioligand binding assay was conducted identically except that the membranes from CHO-CB-2 cells were used.

For a compound to be considered a CB-1 antagonist, the compound must possess a CB-1 receptor binding affinity Ki less than 13000 nM. As determined by the assay described above, the CB-1 receptor binding $K_i$ values of working Examples 1-334 fall within the range of 0.01 nM to 10000 nM.

Cannabinoid Receptor Functional Activity Assay

Functional CB-1 inverse agonist activity of test compounds was determined in CHO-CB-1 cells using a cAMP accumulation assay. CHO-CB-1 cells were grown in 96 well plates to near confluence. On the day of the functional assay, growth medium was aspirated and 100 of Assay Buffer (PBS plus 25 mM HEPES/0.1 mM 3-isobutyl-1-methylxanthine/ 0.1% BSA) was added. Compounds were added to the Assay buffer diluted 1:100 from 100% DMSO and allowed to pre-incubate for 10 minutes prior to addition of 5 uM forskolin. The mixture was allowed to proceed for 15 minutes at room temperature and was terminated by the addition of 0.1 N HCl. The total intracellular cAMP concentration was quantitated using the Amersham cAMP SPA kit.

Utilities and Combinations

Utilities

The compounds of the present invention are cannabinoid receptor modulators, and include compounds which are, for example, selective agonists, partial agonists, inverse agonists, antagonists or partial antagonists of the cannabinoid receptor. Accordingly, the compounds of the present invention may be useful for the treatment or prevention of diseases and disorders associated with G-protein coupled cannabinoid receptor activity. Preferably, compounds of the present invention possess activity as antagonists or inverse agonists of the CB-1 receptor, and may be used in the treatment of diseases or disorders associated with the activity of the CB-1 receptor.

Accordingly, the compounds of the present invention can be administered to mammals, preferably humans, for the treatment of a variety of conditions and disorders, including, but not limited to metabolic and eating disorders as well as conditions associated with metabolic disorders, (e.g., obesity, diabetes, arteriosclerosis, hypertension, polycystic ovary disease, cardiovascular disease, osteoarthritis, dermatological disorders, hypertension, insulin resistance, hypercholesterolemia, hypertriglyceridemia, cholelithiasis and sleep disorders, hyperlipidemic conditions, bulimia nervosa and compulsive eating disorders) or psychiatric disorders, such as substance abuse, depression, anxiety, mania and schizophrenia. These compounds could also be used for the improvement of cognitive function (e.g., the treatment of dementia, including Alzheimer's disease, short term memory loss and attention deficit disorders); neurodegenerative disorders (e.g., Parkinson's Disease, cerebral apoplexy and craniocerebral trauma) and hypotension (e.g., hemorrhagic and endotoxin-inducd hypotension). These compounds could also be used for treatment of catabolism in connection with pulmonary dysfunction and ventilator dependency; treatment of cardiac dysfunction (e.g., associated with valvular disease, myocardial infarction, cardiac hypertrophy or congestive heart failure); and improvement of the overall pulmonary function; transplant rejection; rheumatoid arthritis; multiple sclerosis; inflammatory bowel disease; lupus; graft vs. host disease; T-cell mediated hypersensitivity disease; psoriasis; asthma; Hashimoto's thyroiditis; Guillain-Barre syndrome; cancer; contact dermatitis; allergic rhinitis; and ischemic or reperfusion injury.

Compounds useful in the treatment of appetitive or motivational disorders regulate desires to consume sugars, carbohydrates, alcohol or drugs and more generally to regulate the consumption of ingredients with hedonic value. In the present description and in the claims, appetitive disorders are understood as meaning: disorders associated with a substance and especially abuse of a substance and/or dependency on a substance, disorders of eating behaviors, especially those liable to cause excess weight, irrespective of its origin, for example: bulimia nervosa, craving for sugars. The present invention therefore further relates to the use of a CB-1 receptor antagonist or inverse agonist for the treatment of bulimia and obesity, including obesity associated with type II diabetes (non-insulin-dependent diabetes), or more generally any disease resulting in the patient becoming overweight. Obesity, as described herein, is defined by a body mass index ($kg/m^2$) of at least 26. It may be due to any cause, whether genetic or environmental, including overeating and bulimia, polycycstic ovary disease, craniopharyngeoma, Prader-Willi Syndrome, Frohlich's Syndrome, Type II diabetes, growth hormone deficiency, Turner's Syndrome and other pathological states characterized by reduced metabolic activity or reduced energy expenditure. As used with reference to the utilities described herein, the term "treating" or "treatment" encompasses prevention, partial alleviation, or cure of the disease or disorder. Further, treatment of obesity is expected to prevent progression of medical covariants of obesity, such as arteriosclerosis, Type II diabetes, polycystic ovary disease, cardiovascular disease, osteoarthritis, dermatological disorders, hypertension, insulin resistance, hypercholesterolemia, hypertriglyceridemia, cholelithiasis and sleep disorders.

Compounds in the present invention may also be useful in treating substance abuse disorders, including substance dependence or abuse without physiological dependence. Substances of abuse include alcohol, amphetamines (or amphetamine-like substances), caffeine, cannabis, cocaine, hallucinogens, inhalents, nicotine, opioids, phencyclidine (or phencyclidine-like compounds), sedative-hypnotics or benzodiazepines, and other (or unknown) substances and combinations of the above. The terms "substance abuse disorders" also includes drug or alcohol withdrawal syndromes and substance-induced anxiety or mood disorder with onset during withdrawal.

Compounds in the present invention may be useful in treating memory impairment and cognitive disorders. The condition of memory impairment is manifested by impairment of the ability to learn new information and/or the inability to recall previously learned information. Memory impairment is a primary symptom of dementia and can also be a symptom associated with such diseases as Alzheimer's disease, schizophrenia, Parkinson's disease, Huntington's disease, Pick's disease, Creutzfeld-Jakob disease, HIV, cardiovascular disease, and head trauma as well as age-related cognitive decline. Dementias are diseases that include memory loss and additional intellectual impairment separate from memory. Cannabinoid receptor modulators may also be useful in treating cognitive impairments related to attentional deficits, such as attention deficit disorder.

Compounds in the present invention may also be useful in treating diseases associated with dysfunction of brain dopaminergic systems, such as Parkinson's Disease and substance abuse disorders. Parkinsons's Disease is a neurodenerative movement disorder characterized by bradykinesia and tremor.

As modulators of the cannabinoid receptor, the compounds of the present invention are further useful for the treatment and prevention of respiratory diseases and disorders. Respiratory diseases for which cannabinoid receptor modulators are useful include, but are not limited to, chronic pulmonary obstructive disorder, emphysema, asthma, and bronchitis. In addition, cannabinoid receptor modulators block the activation of lung epithelial cells by moeties such as allergic agents, inflammatory cytokines or smoke, thereby limiting release of mucin, cytokines, and chemokines, or selectively inhibiting lung epithelial cell activation.

Moreover, the compounds employed in the present invention may stimulate inhibitory pathways in cells, particularly in leukocytes, lung epithelial cells, or both, and are thus useful in treating such diseases. "Leukocyte activation" is defined herein as any or all of cell proliferation, cytokine production, adhesion protein expression, and production of inflammatory mediators. "Epithelial cell activation" is defined herein as the production of any or all of mucins, cytokines, chemokines, and adhesion protein expression.

Use of the compounds of the present invention for treating leukocyte activation-associated disorders is exemplified by, but is not limited to, treating a range of disorders such as: transplant (such as organ transplant, acute transplant, xenotransplant or heterograft or homograft (such as is employed in burn treatment)) rejection; protection from ischemic or reperfusion injury such as ischemic or reperfusion injury incurred during organ transplantation, myocardial infarction, stroke or other causes; transplantation tolerance induction; arthritis (such as rheumatoid arthritis, psoriatic arthritis or osteoarthritis); multiple sclerosis; respiratory and pulmonary diseases including but not limited to chronic obstructive pulmonary disease (COPD), emphysema, bronchitis, and acute respiratory distress syndrome (ARDS); inflammatory bowel disease, including ulcerative colitis and Crohn's disease; lupus (systemic lupus erythematosis); graft vs. host disease; T-cell mediated hypersensitivity diseases, including contact hypersensitivity, delayed-type hypersensitivity, and gluten-sensitive enteropathy (Celiac disease); psoriasis; contact dermatitis (including that due to poison ivy); Hashimoto's thyroiditis; Sjogren's syndrome; Autoimmune Hyperthyroidism, such as Graves' Disease; Addison's disease (autoimmune disease of the adrenal glands); Autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; glomerulonephritis; serum sickness; uticaria; allergic diseases such as respiratory allergies (asthma, hayfever, allergic rhinitis) or skin allergies; scleracierma; mycosis fungoides; acute inflammatory and respiratory responses (such as acute respiratory distress syndrome and ishchemia/reperfusion injury); dermatomyositis; alopecia areata; chronic actinic dermatitis; eczema; Behcet's disease; Pustulosis palmoplanteris; Pyoderma gangrenum; Sezary's syndrome; atopic dermatitis; systemic schlerosis; and morphea. The term "leukocyte activation-associated" or "leukocyte-activation mediated" disease as used herein includes each of the above referenced diseases or disorders. In a particular embodiment, the compounds of the present invention are useful for treating the aforementioned exemplary disorders irrespective of their etiology. The combined activity of the present compounds towards monocytes, macrophages, T-cells, etc. may be useful in treating any of the above-mentioned disorders.

Cannabinoid receptors are important in the regulation of Fc gamma receptor responses of monocytes and macrophages. Compounds of the present invention inhibit the Fc gamma dependent production of TNF alpha in human monocytes/ macrophages. The ability to inhibit Fc gamma receptor dependent monocyte and macrophage responses results in additional anti-inflammatory activity for the present compounds. This activity is especially of value, for example, in treating inflammatory diseases such as arthritis or inflammatory bowel disease. In particular, the present compounds are useful for treating autoimmune glomerulonephritis and other instances of glomerulonephritis induced by deposition of immune complexes in the kidney that trigger Fc gamma receptor responses leading to kidney damage.

Cannabinoid receptors are expressed on lung epithelial cells. These cells are responsible for the secretion of mucins and inflammatory cytokines/chemokines in the lung and are thus intricately involved in the generation and progression of respiratory diseases. Cannabinoid receptor modulators regulate both the spontaneous and the stimulated production of both mucins and cytokines. Thus, such compounds are useful in treating respiratory and pulmonary diseases including, COPD, ARDS, and bronchitis.

Further, cannabinoid receptors may be expressed on gut epithelial cells and hence regulate cytokine and mucin production and may be of clinical use in treating inflammatory diseases related to the gut. Cannabinoid receptors are also expressed on lymphocytes, a subset of leukocytes. Thus, cannabinoid receptor modulators will inhibit B and T-cell activation, proliferation and differentiation. Thus, such compounds will be useful in treating autoimmune diseases that involve either antibody or cell mediated responses such as multiple sclerosis and lupus.

In addition, cannabinoid receptors regulate the Fc epsilon receptor and chemokine induced degranulation of mast cells and basophils. These play important roles in asthma, allergic rhinitis, and other allergic disease. Fc epsilon receptors are stimulated by IgE-antigen complexes. Compounds of the present invention inhibit the Fc epsilon induced degranulation responses, including the basophil cell line, RBL. The ability to inhibit Fc epsilon receptor dependent mast cell and basophil responses results in additional anti-inflammatory and anti-allergic activity for the present compounds. In particular, the present compounds are useful for treating asthma, allergic rhinitis, and other instances of allergic disease.

Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other suitable therapeutic agents useful in the treatment of the aforementioned disorders including: anti-obesity agents; anti-diabetic agents, appetite suppressants; cholesterol/lipid-lowering agents, HDL-raising agents, cognition enhancing agents, agents used to treat neurodegeneration, agents used to treat respiratory conditions, agents used to treat bowel disorders, anti-inflammatory agents; anti-anxiety agents; anti-depressants; anti-hypertensive agents; cardiac glycosides; and anti-tumor agents.

Such other therapeutic agent(s) may be administered prior to, simultaneously with, or following the administration of the cannabinoid receptor modulators in accordance with the invention.

Examples of suitable anti-obesity agents for use in combination with the compounds of the present invention include melanocortin receptor (MC4R) agonists, melanin-concentrating hormone receptor (MCHR) antagonists, growth hormone secretagogue receptor (GHSR) antagonists, galanin receptor modulators, orexin antagonists, CCK agonists, GLP-1 agonists, and other Pre-proglucagon-derived peptides; NPY1 or NPY5 antagonsist, NPY2 and NPY4 modulators, corticotropin releasing factor agonists, histamine receptor-3 (H3) modulators, aP2 inhibitors, PPAR gamma modulators, PPAR delta modulators, acetyl-CoA carboxylase (ACC) inihibitors, 11-β-HSD-1 inhibitors, adinopectin receptor modulators; beta 3 adrenergic agonists, such as AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, a thyroid receptor beta modulator, such as a thyroid receptor ligand as disclosed in WO 97/21993 (U. Cal SF), WO 99/00353 (KaroBio) and GB98/284425 (KaroBio), a lipase inhibitor, such as orlistat or ATL-962 (Alizyme), serotonin receptor agonists, (e.g., BVT-933 (Biovitrum)), monoamine reuptake inhibitors or releasing agents, such as fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazindol, anorectic agents such as topiramate (Johnson & Johnson), CNTF (ciliary neurotrophic factor)/Axokine® (Regeneron), BDNF (brain-derived neurotrophic factor), leptin and leptin receptor modulators, or cannabinoid-1 receptor antagonists, such as SR-141716 (Sanofi) or SLV-319 (Solvay).

Examples of suitable anti-diabetic agents for use in combination with the compounds of the present invention include: insulin secretagogues or insulin sensitizers, which may include biguanides, sulfonyl ureas, glucosidase inhibitors, aldose reductase inhibitors, PPAR γ agonists such as thiazolidinediones, PPAR α agonists (such as fibric acid derivatives), PPAR δ antagonists or agonists, PPAR α/γ dual agonists, 11-β-HSD-1 inhibitors, dipeptidyl peptidase IV (DP4) inhibitors, SGLT2 inhibitors, glycogen phosphorylase inhibitors, and/or meglitinides, as well as insulin, and/or glucagon-like peptide-1 (GLP-1), GLP-1 agonist, and/or a PTP-1B inhibitor (protein tyrosine phosphatase-1B inhibitor).

The antidiabetic agent may be an oral antihyperglycemic agent preferably a biguanide such as metformin or phenformin or salts thereof, preferably metformin HCl. Where the antidiabetic agent is a biguanide, the compounds of the present invention will be employed in a weight ratio to biguanide within the range from about 0.001:1 to about 10:1, preferably from about 0.01:1 to about 5:1.

The antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the beta-cells, with glyburide and glipizide being preferred, which may be administered in the same or in separate oral dosage forms. The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of the present invention may be employed in combination with a PPAR γ agonist such as a thiazolidinedione oral anti-diabetic agent or other insulin sensitizers (which has an insulin sensitivity effect in NIDDM patients) such as rosiglitazone (SKB), pioglitazone (Takeda), Mitsubishi's MCC-555 (disclosed in U.S. Pat. No. 5,594,016), Glaxo-Welcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi), preferably rosiglitazone and pioglitazone.

The compounds of the present invention may be employed with a PPARα/γ dual agonist such as MK-767/KRP-297 (Merck/Kyorin; as described in, K. Yajima, et. al., *Am. J. Physiol. Endocrinol. Metab.,* 284: E966-E971 (2003)), AZ-242 (tesaglitazar; Astra-Zeneca; as described in B. Ljung, et. al., *J. Lipid Res.,* 43, 1855-1863 (2002)); muraglitazar; or the compounds described in U.S. Pat. No. 6,414,002.

The compounds of the present invention may be employed in combination with anti-hyperlipidemia agents, or agents used to treat arteriosclerosis. An example of an hypolipidemic agent would be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, pitavastatin (Nissan/Sankyo's nisvastatin (NK-104) or itavastatin), disclosed in U.S. Pat. No. 5,011,930, Shionogi-Astra/Zeneca rosuvastatin (visastatin (ZD-4522)) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No.0,142,146 A2, and quinoline and pyridine derivatives disclosed in U.S. Pat. Nos. 5,506,219 and 5,691,322. In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller, et al., *J. Med. Chem.,* 31, 1869-1871 (1998) including isoprenoid (phosphinyl-methyl)phosphonates as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., *Current Pharmaceutical Design,* 2, 1-40 (1996).

In addition, other squalene synthetase inhibitors suitable for use herein include the terpenoid pyrophosphates disclosed by P. Ortiz de Montellano, et al., *J. Med. Chem.,* 20, 243-249 (1977), the farnesyl diphosphate analog A and presqualene pyrophosphate (PSQ-PP) analogs as disclosed by Corey and Volante, *J. Am. Chem. Soc.,* 98, 1291-1293 (1976), phosphinylphosphonates reported by McClard, R. W. et al., *J. Am. Chem. Soc.,* 109, 5544 (1987) and cyclopropanes reported by Capson, T. L., PhD dissertation, June, 1987, Dept. Med. Chem. U of Utah, Abstract, Table of Contents, pp 16, 17, 40-43, 48-51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (SEC-HOLEX, POLICEXIDE) and cholestagel (Sankyo/Geltex), as well as lipostabil (Rhone-Poulenc), Poulenc), Eisai E-5050 (an N-substituted ethanolarnine derivative), imanixil (HOE-402), tetrahydrolipstatin (THL), istigmastanylphos-phoryl-choline (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The other hypolipidemic agent may be an ACAT inhibitor (which also has anti-atherosclerosis activity) such as disclosed in, *Drugs of the Future,* 24, 9-15 (1999), (Avasimibe); "The ACAT inhibitor, C1-1011 is effective in the prevention and regression of aortic fatty streak area in hamsters", Nicolosi et al., *Atherosclerosis* (Shannon, Irel), 137 (1), 77-85 (1998); "The pharmacological profile of FCE 27677: a novel ACAT inhibitor with potent hypolipidemic activity mediated by selective suppression of the hepatic secretion of ApoB 100-containing lipoprotein", Ghiselli, Giancarlo, *Cardiovasc. Drug Rev.,* 16 (1), 16-30 (1998); "RP 73163: a bioavailable alkylsulfinyl-diphenylimidazole ACAT inhibitor", Smith, C., et al., *Bioorg. Med. Chem. Lett,* 6 (1), 47-50 (1996); "ACAT inhibitors: physiologic mechanisms for hypolipidemic and anti-atherosclerotic activities in experimental animals", Krause et al., Editor(s): Ruffolo, Robert R., Jr.; Hollinger, Mannfred A., *Inflammation: Mediators Pathways,* 173-98 (1995), Publisher: CRC, Boca Raton, Fla.; "ACAT inhibitors: potential anti-atherosclerotic agents", Sliskovic et al., *Curr. Med. Chem.,* 1 (3), 204-25 (1994); "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)-methyl]ureas with enhanced hypocholesterolemic activity", Stout et al., *Chemtracts: Org. Chem.,* 8 (6), 359-62 (1995), or TS-962 (Taisho Pharmaceutical Co. Ltd), as well as F-1394, CS-505, F-12511, HL-004, K-10085 and YIC-C8-434.

The hypolipidemic agent may be an upregulator of LDL receptor activity such as MD-700 (Taisho Pharmaceutical Co. Ltd) and LY295427 (Eli Lilly). The hypolipidemic agent may be a cholesterol absorption inhibitor preferably Schering-Plough's SCH48461 (ezetimibe) as well as those disclosed in *Atherosclerosis* 115, 45-63 (1995) and *J. Med. Chem.* 41, 973 (1998).

The other lipid agent or lipid-modulating agent may be a cholesteryl transfer protein inhibitor (CETP) such as Pfizer's CP-529,414 as well as those disclosed in WO/0038722 and in EP 818448 (Bayer) and EP 992496, and Pharmacia's SC-744 and SC-795, as well as CETi-1 and JTT-705.

The hypolipidemic agent may be an ileal $Na^+$/bile acid cotransporter inhibitor such as disclosed in Drugs of the Future, 24, 425-430 (1999). The ATP citrate lyase inhibitor which may be employed in the combination of the invention may include, for example, those disclosed in U.S. Pat. No. 5,447,954.

The other lipid agent also includes a phytoestrogen compound such as disclosed in WO 00/30665 including isolated soy bean protein, soy protein concentrate or soy flour as well as an isoflavone such as genistein, daidzein, glycitein or equol, or phytosterols, phytostanol or tocotrienol as disclosed in WO 2000/015201; a beta-lactam cholesterol absorption inhibitor such as disclosed in EP 675714; an HDL upregulator such as an LXR agonist, a PPAR α-agonist and/or an FXR agonist; an LDL catabolism promoter such as disclosed in EP 1022272; a sodium-proton exchange inhibitor such as disclosed in DE 19622222; an LDL-receptor inducer or a steroidal glycoside such as disclosed in U.S. Pat. No. 5,698,527 and GB 2304106; an anti-oxidant such as beta-carotene, ascorbic acid, α-tocopherol or retinol as disclosed in WO 94/15592 as well as Vitamin C and an antihomocysteine agent such as folic acid, a folate, Vitamin B6, Vitamin B12 and Vitamin E; isoniazid as disclosed in WO 97/35576; a cholesterol absorption inhibitor, an HMG-CoA synthase inhibitor, or a lanosterol demethylase inhibitor as disclosed in WO 97/48701; a PPAR δ agonist for treating dyslipidemia; or a sterol regulating element binding protein-I (SREBP-1) as disclosed in WO 2000/050574, for example, a sphingolipid, such as ceramide, or neutral sphingomyelenase (N-SMase) or fragment thereof. Preferred hypolipidemic agents are pravastatin, lovastatin, simvastatin, atorvastatin, fluvastatin, pitavastatin and rosuvastatin, as well as niacin and/or cholestagel.

The compounds of the present invention may be employed in combination with anti-hypertensive agents. Examples of suitable anti-hypertensive agents for use in combination with the compounds of the present invention include beta adrenergic blockers, calcium channel blockers (L-type and/or T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Cannbinoid receptor modulators could be useful in treating other diseases associated with obesity, including sleep disorders. Therefore, the compounds described in the present invention could be used in combination with therapeutics for treating sleep disorders. Examples of suitable therapies for treatment of sleeping disorders for use in combination with the compounds of the present invention include melatonin analogs, melatonin receptor antagonists, ML 1 B agonists, GABA receptor modulators; NMDA receptor modulators, histamine-3 (H3) receptor modulators, dopamine agonists and orexin receptor modulators.

Cannabinoid receptor modulators may reduce or ameliorate substance abuse or addictive disorders. Therefore, combination of cannabinoid receptor modulators with agents used to treat addictive disorders may reduce the dose requirement or improve the efficacy of current addictive disorder therapeutics. Examples of agents used to treat substance abuse or addictive disorders are: selective serotonin reuptake inhibitors (SSRI), methadone, buprenorphine, nicotine and bupropion.

Cannabinoid receptor modulators may reduce anxiety or depression; therefore, the compounds described in this application may be used in combination with anti-anxiety agents or antidepressants. Examples of suitable anti-anxiety agents for use in combination with the compounds of the present invention include benzodiazepines (e.g., diazepam, lorazepam, oxazepam, alprazolam, chlordiazepoxide, clonazepam, chlorazepate, halazepam and prazepam), 5HT1A receptor agonists (e.g., buspirone, flesinoxan, gepirone and ipsapirone), and corticotropin releasing factor (CRF) antagonists.

Examples of suitable classes of anti-depressants for use in combination with the compounds of the present invention include norepinephrine reuptake inhibitors (tertiary and secondary amine tricyclics), selective serotonin reuptake inhibitors (SSRIs) (fluoxetine, fluvoxamine, paroxetine and sertraline), monoamine oxidase inhibitors (MAOIs) (isocarboxazid, phenelzine, tranylcypromine, selegiline), reversible inhibitors of monoamine oxidase (RIMAs) (moclobemide), serotonin and norepinephrine reuptake inhibitors (SNRIs) (venlafaxine), corticotropin releasing factor (CRF) receptor antagonists, alpah-adrenoreceptor antagonists, and atypical antidepressants (bupropion, lithium, nefazodone, trazodone and viloxazine).

The combination of a conventional antipsychotic drug with a CB-1 receptor antagonist could also enhance symptom reduction in the treatment of psychosis or mania. Further, such a combination could enable rapid symptom reduction, reducing the need for chronic treatment with antipsychotic agents. Such a combination could also reduce the effective antipsychotic dose requirement, resulting in reduced probability of developing the motor dysfunction typical of chronic antipsychotic treatment.

Examples of suitable antipsychotic agents for use in combination with the compounds of the present invention include the phenothiazine (chlorpromazine, mesoridazine, thioridazine, acetophenazine, fluphenazine, perphenazine and trifluoperazine), thioxanthine (chlorprothixene, thiothixene), heterocyclic dibenzazepine (clozapine, olanzepine and aripiprazole), butyrophenone (haloperidol), dipheyylbutylpiperidine (pimozide) and indolone (molindolone) classes of antipsychotic agents. Other antipsychotic agents with potential therapeutic value in combination with the compounds in the present invention include loxapine, sulpiride and risperidone.

Combination of the compounds in the present invention with conventional antipsychotic drugs could also provide an enhanced therapeutic effect for the treatment of schizophrenic disorders, as described above for manic disorders. As used here, schizophrenic disorders include paranoid, disorganized, catatonic, undifferentiated and residual schizophrenia, schizophreniform disorder, shcizoaffective disorder, delusional disorder, brief psychotic disorder and psychotic disorder not specified. Examples of suitable antipsychotic drugs for combination with the compounds in the present invention include the antipsychotics mentioned above, as well as dopamine receptor antagonists, muscarinic receptor agonists, 5HT2A receptor antagonists and 5HT2A/dopamine receptor antagonists or partial agonists (e.g., olanzepine, aripiprazole, risperidone, ziprasidone).

The compounds described in the present invention could be used to enhance the effects of cognition-enhancing agents, such as acetylcholinesterase inhibitors (e.g., tacrine), muscarinic receptor-1 agonists (e.g., milameline), nicotinic agonists, glutamic acid receptor (AMPA and NMDA) modulators, and nootropic agents (e.g., piracetam, levetiracetam). Examples of suitable therapies for treatment of Alzheimer's disease and cognitive disorders for use in combination with the compounds of the present invention include donepezil, tacrine, revastigraine, 5HT6, gamma secretase inhibitors, beta secretase inhibitors, SK channel blockers, Maxi-K blockers, and KCNQs blockers.

The compounds described in the present invention could be used to enhance the effects of agents used in the treatment of Parkinson's Disease. Examples of agents used to treat Parkinson's Disease include: levadopa with or without a COMT inhibitor, antiglutamatergic drugs (amantadine, riluzole), alpha-2 adrenergic antagonists such as idazoxan, opiate antagonists, such as naltrexone, other dopamine agonists or transportor modulators, such as ropinirole, or pramipexole or neurotrophic factors such as glial derived neurotrophic factor (GDNF).

The compounds described in the present invention could be used in combination with suitable anti-inflammatory agents. Examples of suitable anti-inflammatory agents for use in combination with the compounds of the present invention include prednisone, dexamethasone, cyclooxygenase inhibitors (i.e., COX-1 and/or COX-2 inhibitors such as NSAIDs, aspirin, indomethacin, ibuprofen, piroxicam, Naproxen®, Celebrex®, Vioxx®), CTLA4-Ig agonists/antagonists, CD40 ligand antagonists, IMPDH inhibitors, such as mycophenolate (CellCept®), integrin antagonists, alpha-4 beta-7 integrin antagonists, cell adhesion inhibitors, interferon gamma antagonists, ICAM-1, tumor necrosis factor (TNF) antagonists (e.g., infliximab, OR1384, including TNF-alpha inhibitors, such as tenidap, anti-TNF antibodies or soluble TNF receptor such as etanercept (Enbrel®), rapamycin (sirolimus or Rapamune) and leflunomide (Arava)), prostaglandin synthesis inhibitors, budesonide, clofazimine, CNI-1493, CD4 antagonists (e.g., priliximab), p38 mitogen-activated protein kinase inhibitors, protein tyrosine kinase (PTK) inhibitors, IKK inhibitors, and therapies for the treatment of irritable bowel syndrome (e.g., Zelnorm® and Maxi-K® openers such as those disclosed in U.S. Pat. No. 6,184,231 B1).

Exemplary of such other therapeutic agents which may be used in combination with cannabinoid receptor modulators include the following: cyclosporins (e.g., cyclosporin A), anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and gp39, such as antibodies specific for CD40 and/or gp39 (i.e., CD154), fusion proteins constructed from CD40 and gp39 (CD40Ig and CD8gp39), inhibitors, such as nuclear translocation inhibitors, of NF-kappa B function, such as deoxyspergualin (DSG), gold compounds, antiproliferative agents such as methotrexate, FK506 (tacrolimus, Prograf), mycophenolate mofetil, cytotoxic drugs such as azathiprine and cyclophosphamide, anticytokines such as antiIL-4 or IL-4 receptor fusion proteins and PDE 4 inhibitors such as Ariflo, and the PTK inhibitors disclosed in the following U.S. patent applications, incorporated herein by reference in their entirety: Ser. No. 09/097,338, filed Jun. 15, 1998; Ser. No. 09/094,797, filed Jun. 15, 1998; Ser. No. 09/173,413, filed Oct. 15, 1998; and Ser. No. 09/262,525, filed Mar. 4, 1999. See also the following documents and references cited therein and incorporated herein by reference: Hollenbaugh, D., et al., "Cleavable CD40Ig Fusion Proteins and the Binding to Sgp39", *J. Immunol. Methods* (Netherlands), 188 (1), pp. 1-7 (Dec. 15, 1995); Hollenbaugh, D., et al., "The Human T Cell Antigen Gp39, A Member of the TNF Gene Family, Is a Ligand for the CD40 Receptor: Expression of a Soluble Form of Gp39 with B Cell Co-Stimulatory Activity", *EMBO J* (England), 11 (12), pp. 4313-4321 (December 1992); and Moreland, L. W. et al., "Treatment of Rheumatoid Arthritis with a Recombinant Human Tumor Necrosis Factor Receptor (P75)-Fc Fusion Protein," *New England J. of Medicine*, 337 (3), pp. 141-147 (1997).

The above other therapeutic agents, when employed in combination with the compounds of the present invention, may be used, for example, in those amounts indicated in the Physicians' Desk Reference (PDR) or as otherwise determined by one of ordinary skill in the art.

The compounds of formula (1) of the invention can be administered orally or parenterally, such as subcutaneously or intravenously, as well as by nasal application, rectally or sublingually to various mammalian species known to be subject to such maladies, e.g., humans, in an effective amount up to 1 gram, preferably up to 200 mg, more preferably to 50 mg in a regimen of single, two or four divided daily doses.

The compounds of the formula (I) can be administered for any of the uses described herein by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compounds of formula (I) can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Exemplary compositions for nasal aerosol or inhalation administration include solutions in saline which can contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for rectal administration include suppositories which can contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition.

It should be understood that while this invention has been described herein in terms of specific embodiments set forth in detail, such embodiments are presented by way of illustration of the general principles of the invention, and the invention is not necessarily limited thereto. Certain modifications and variations in any given material, process step or chemical formula will be readily apparent to those skilled in the art without departing from the true spirit and scope of the present invention, and all such modifications and variations should be considered within the scope of the claims that follow.

What is claimed is:

1. A compound of formula I:

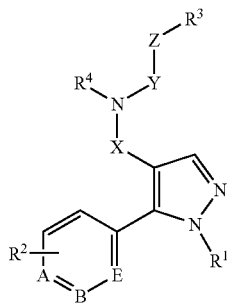

including all pharmaceutically acceptable salts and stereoisomers, wherein:

$R^1$ is selected from the group consisting of hydrogen, alkyl, cycloalkyl, cycloalkylalkyl, heterocyclyl, heterocycloalkyl, aryl, heteroaryl, arylalkyl and heteroarylalkyl;

$R^2$ is selected from the group consisting of 3-halo, 3-aryl, 3-heteroaryl, 3-alkyl, 3-CN, 4-halo, 4-aryl, 4-heteroaryl, 4-alkyl, and -4-CN;

$R^3$ is selected from the group consisting of hydrogen, alkyl, cycloalkyl, cycloalkylalkyl, heterocyclyl, heterocycloalkyl, aryl, heteroaryl, arylalkyl and heteroarylalkyl; with the provisos that when $R^4$ is methyl or ethyl, $R^3$ is not ethyl;

$R^4$ is selected from the group consisting of hydrogen, alkyl, cycloalkyl, cycloalkylalkyl, heterocyclyl, heterocycloalkyl, aryl, heteroaryl, arylalkyl and heteroarylalkyl; or $R^3$ and $R^4$ can be taken together to form cycloalkyl or heterocyclyl;

$R^5$ selected from the group consisting of hydrogen, alkyl, cycloalkyl, cycloalkylalkyl, heterocyclyl, heterocycloalkyl, aryl, heteroaryl, arylalkyl and heteroarylalkyl;

A, B and E are independently selected from the group consisting of C and N, wherein at least one of A, B and E must be C;

X is selected from the group consisting of CO, $SO_2$ and $(CH_2)_n$;

Y is selected from the group consisting of a direct bond, $SO_2$, CO, C=NH, C=N—CN and C=NR$^5$;

Z is selected from the group consisting of a direct bond, NR$^6$ and O, with the proviso that when Y is a direct bond, Z is also a direct bond;

$R^6$ is selected from the group consisting of hydrogen, alkyl, cycloalkyl, cycloalkylalkyl, heterocyclyl, heterocycloalkyl, aryl, heteroaryl, arylalkyl and heteroarylalkyl; and n is an integer of 0 or 1.

2. The compound according to claim 1, wherein:

$R^1$ is selected from the group consisting of aryl, heteroaryl, arylalkyl, and heteroarylalkyl;

$R^2$ is selected from the group consisting of 4-aryl, 4-heteroaryl, 4-Br, 4-Cl, 4-CF$_3$, 3-CF$_3$, 4-CN and Y is a direct bond; and Z is a direct bond.

3. The compound according to claim 2, wherein:

$R^1$ is selected from the group consisting of aryl, heteroaryl, arylalkyl, and heteroarylalkyl substituted with F, Cl, Br, Me, Et, CF$_3$ in any position or combination therein;

$R^2$ is selected from the group consisting of 4-aryl, 4-heteroaryl, 4-Br, 4-Cl, 4-CF$_3$, 3-CF$_3$, 4-CN and any combination therein;

$R^3$ is selected from hydrogen, alkyl, cycloalkyl, cycloalkylalkyl, heterocyclyl, heterocycloalkyl, aryl, heteroaryl, arylalkyl, heteroarylalkyl,

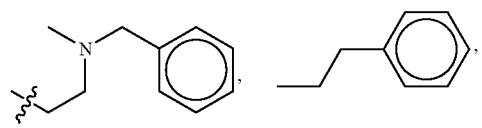

-continued
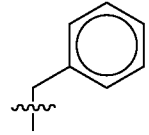
R³ and R⁴ can be taken together to form cycloalkyl, heterocyclyl,
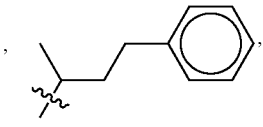
A, B and E are C;
X is CO or (CH₂)ₙ; and
n is 1.
4. The compound according to claim 1, wherein: the compound is selected from
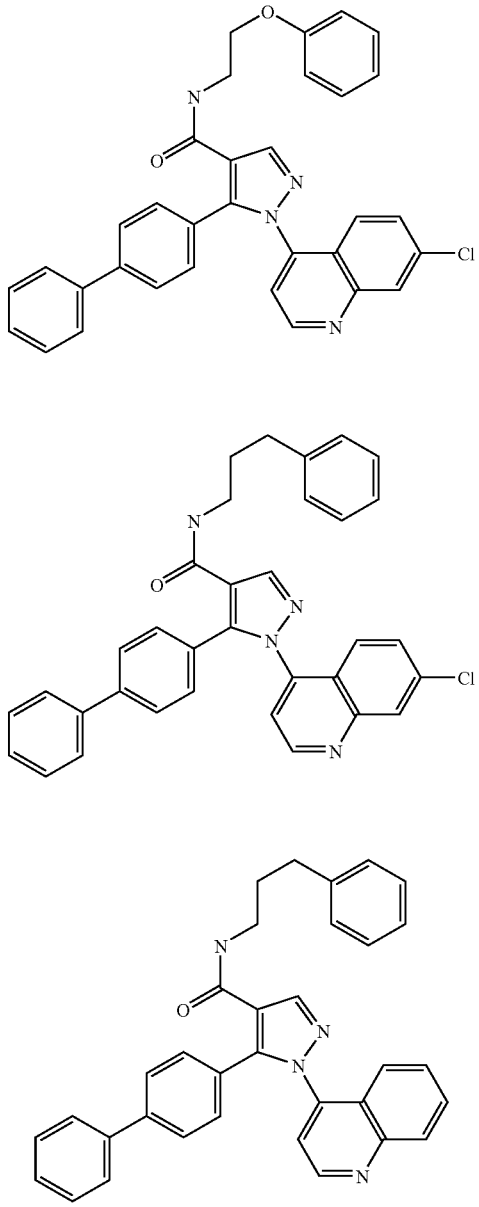
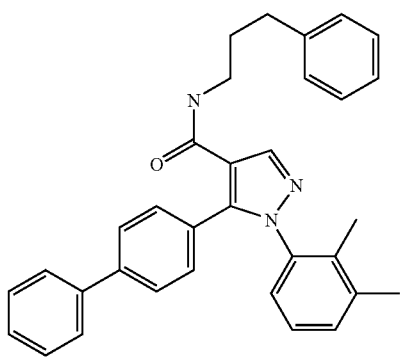

-continued
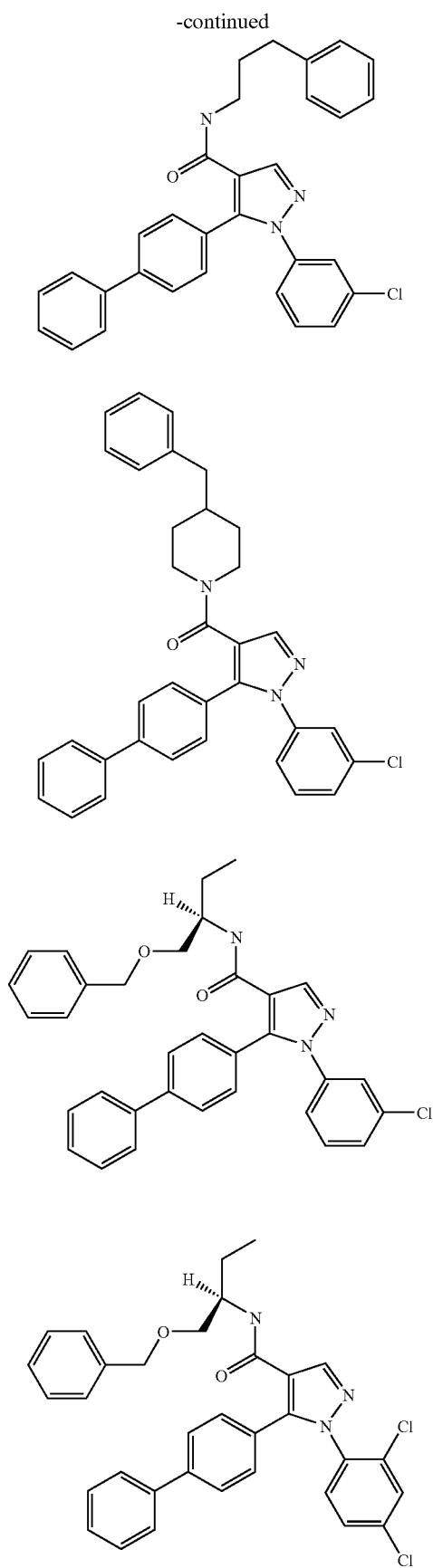
-continued
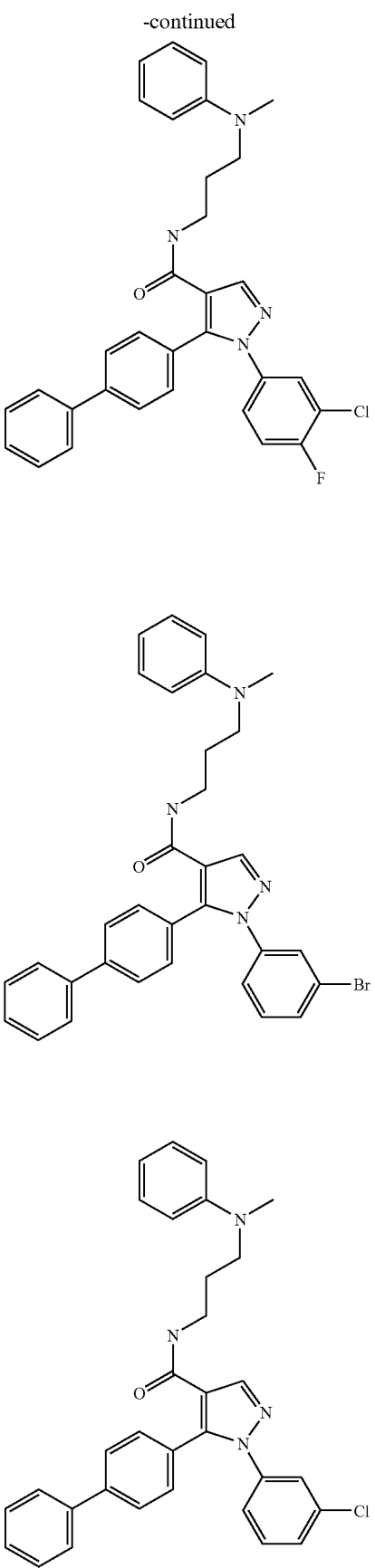

-continued

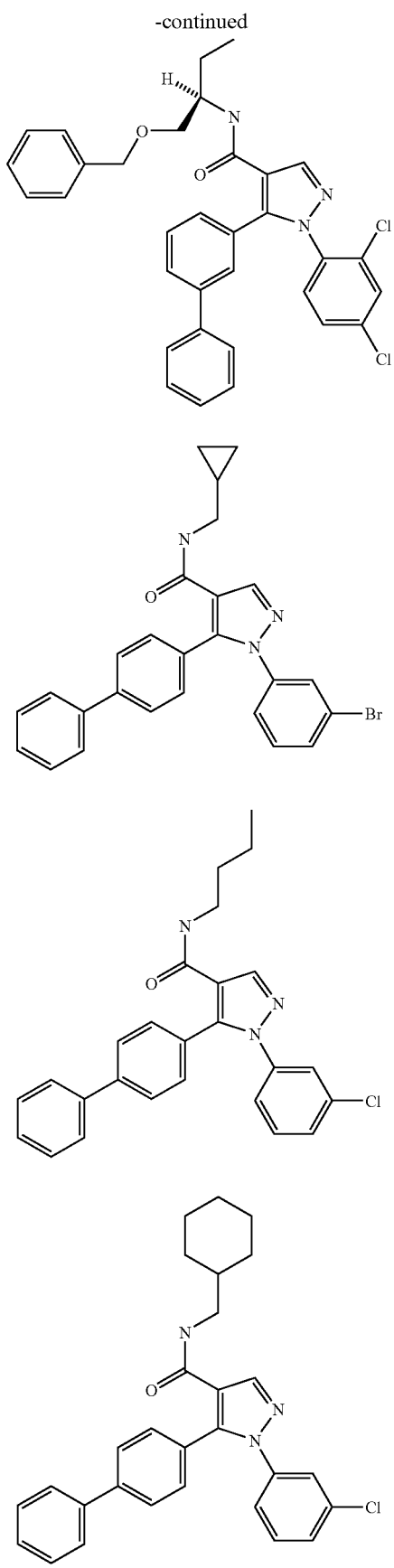

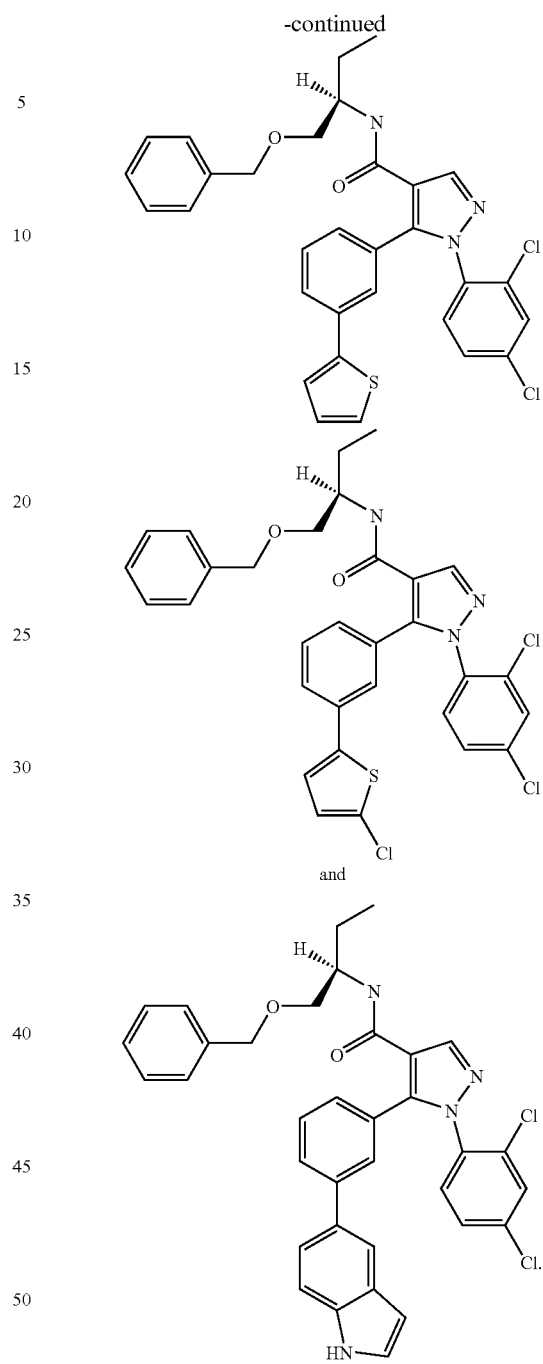

and

5. A pharmaceutical composition, comprising:
at least one compound according to claim 1; and at least one pharmaceutically acceptable carrier or diluent.

6. A pharmaceutical combination, comprising:
at least one compound according to claim 1;
at least one additional therapeutic agent selected from the group consisting of anti-obesity agents; appetite suppressants; anti-diabetic agents; anti-hyperlipidemia agents; hypolipidemic agents; hypocholesterolemic agents; lipid-modulating agents; cholesterol-lowering agents; lipid-lowering agents; and anti-hypertensive agents; and
at least one pharmaceutically acceptable carrier or diluent.

7. The pharmaceutical combination according to claim 6, wherein, the additional therapeutic agent may be administered prior to, simultaneously with, or following the administration of the pharmaceutical composition.

8. The pharmaceutical combination according to claim 6, wherein, the anti-obesity agent is selected from melanocortin receptor (MC4R) agonists; melanin-concentrating hormone receptor (MCHR) antagonists; growth hormone secretagogue receptor (GHSR) antagonists; orexin antagonists; CCK agonists; GLP-1 agonists and other Pre-proglucagon-derived peptides; NPY1 or NPY5 antagonists; NPY2 and NPY4 modulators; corticotropin releasing factor agonists; histamine receptor-3 (H3) modulators; aP2 inhibitors; PPAR gamma modulators; PPAR delta modulators; acetyl-CoA carboxylase (ACC) inhibitors, adiponectin receptor modulators, beta 3 adrenergic agonists, including AJ9677, L750355 and CP331648 or other known beta 3 agonists; thyroid receptor beta modulator; lipase inhibitors, including orlistat and ATL-962; serotonin receptor agonists, including BVT-933; monoamine reuptake inhibitors or releasing agents, including fenfluramine, dexfenfluramine, fluvoxamine, fluoxetine, paroxetine, sertraline, chiorphentermine, cloforex, clortermine, picilorex, sibutramine, dexamphetamine, phentermine, phenylpropanolamine and mazindol; anorectic agents, including topiramate; ciliary neurotrophic factor, including Axokine; brain-derived neurotrophic factor; leptin and other cannabinoid-1 receptor antagonists, including SR-141716 and SLV-319.

9. The pharmaceutical combination according to claim 6, wherein, the anti-diabetic agent is selected from insulin secretagogues; insulin sensitizers; anti-hyperglycemic agents; biguanides; sulfonyl ureas; glucosidase inhibitors; aldose reductase inhibitors; PPAR γ agonists including thiazolidinediones; PPAR α agonists, including fibric acid derivatives; PPAR δ antagonists or agonists; PPAR α/γ dual agonists; dipeptidyl peptidase IV inhibitors; SGLT2 inhibitors; glycogen phosphorylase inhibitors; meglitinides; insulin; glucagon-like peptide-1; glucagon-like peptide 1 agonists; and protein tyrosine phosphatase-1B inhibitor.

10. The pharmaceutical combination according to claim 9, wherein the anti-diabetic agent is an oral antihyperglycemic agent selected from biguanide, metformin, phenformin, metformin HCl and other salts thereof.

11. The pharmaceutical combination according to claim 10 wherein, the anti-diabetic agent is a biguanide and the compound of claim 1 will be administered in a weight ratio to the biguanide within the range from about 0.001:1 to about 10:1.

12. The pharmaceutical combination according to claim 11 wherein, the anti-diabetic agent is a biguanide and the compound of claim 1 will be administered in a weight ratio to the biguanide within the range from about 0.01:1 to about 5:1.

13. The pharmaceutical combination according to claim 9 wherein, the sulfonyl ureas are selected from glyburide, glibenclamide, glimepiride, glipizide, gliclazide, chiorpropamide and other known sulfonylureas or other antihyperglycemic agents which act on the ATP-dependent channel of the beta-cells.

14. The pharmaceutical combination according to claim 13 wherein, the combination of the compound of claim 1 and the sulfonyl urea is administered in the same or separate oral dosage forms.

15. The pharmaceutical combination according to claim 9 wherein, the glucosidase inhibitor is selected from acarbose and miglitol.

16. The pharmaceutical combination according to claim 15 wherein, the combination of the compound of claim 1 and the glucosidase inhibitor is administered in the same or separate oral dosage forms.

17. The pharmaceutical combination according to claim 9 wherein, the PPARγ agonist is a thiazolidinedione oral antidiabetic agent.

18. The pharmaceutical combination according to claim 9 wherein, the insulin sensitizer is selected from rosiglitazone; pioglitazone; MCC-555; GL-262570, englitazone; darglitazone; isaglitazone; JTT-501; L-895645; R-119702; NN-2344; and YM-440.

19. The pharmaceutical combination according to claim 9 wherein, the PPARα/γ dual agonists are selected from MK-767/KRP-297; tesaglitazar and muraglitazar.

20. The pharmaceutical combination according to claim 6 wherein, the hypolipidemic agent is an HMG CoA reductase inhibitor selected from mevastatin; compounds related to mevastatin; lovastatin; mevinolin; compounds related to lovastatin and mevinolin; pravastatin and compounds related to pravastatin; simvastatin and compounds related to simvastatin; fluvastatin; cerivastatin; atorvastatin; pitavastatin; nisvastatin; itavastatin; rosuvastatin; visastatin; compounds related to rosuvastatin and visastatin; pyrazole analogs of mevalonolactone derivatives; indene analogs of mevalonolactone derivatives; 6-[2-(substituted-pyrrol-1-yl)-alkyl)pyran-2-ones and derivatives thereof; SC-45355; 3-substituted pentanedioic acid derivative; dichioroacetate; imidazole analogs of mevalonolactone; 3-carboxy-2-hydroxy-propanephosphonic acid derivatives; 2,3-disubstituted pyrrole, furan and thiophene derivatives; naphthyl analogs of mevalonolactone; octahydronaphthalenes; keto analogs of lovastatin and mevinolin; quinoline and pyridine derivatives; and phosphinic acid compounds.

21. The pharmaceutical combination according to claim 6 wherein, the hypolipidemic agent is a squalene synthetase inhibitor selected from α-phosphono-sulfonates, isoprenoid (phosphinyl-methyl) phosphonates, terpenoid pyrophosphates, farnesyl diphosphate analog A and presqualene pyrophosphate analogs, phosphinyiphosphonates and cyclopropanes.

22. The pharmaceutical combination according to claim 6 wherein, the hypolipidemic agent is a fibric acid derivative selected from fenofibrate, gemfibrozil, clofibrate, bezafibrate, ciprofibrate, clinofibrate, probucol and compounds related to probucol.

23. The pharmaceutical combination according to claim 6 wherein, the hypolipidemic agent is a bile acid sequestrant selected from cholestyramine, colestipol, DEAE-Sephadex, Secholex, Policexide, cholestagel, lipostabil, E-5050, N-substituted ethanolamine derivatives, imanixil, tetrahydrolipstatin, istigmastanylphos-phorylcholine, aminocyclodextrin, AJ-814, azulene derivatives, melinamide, 58-035, CL-277, 082, CL-283,546, disubstituted urea derivatives, nicotinic acid, niacin, acipimox, acifran, neomycin, p-aminosalicylic acid, aspirin, poly(diallylmethylamine) derivatives, quaternary amine poly(diallyl)dimethylammonium chloride, ionenes and other known serum cholesterol lowering agents.

24. The pharmaceutical combination according to claim 6 wherein, the hypolipidemic agent is an acyl CoA:cholesterol O-acyl transferase inhibitor selected from substituted N-phenyl-N'-[(1-phenylcyclopentyl)methyl]ureas; TS-962; F-1394; CS-505; F-12511; HL-004; K-10085; and YIC-C8-434.

25. The pharmaceutical combination according to claim 6 wherein, the hypolipidemic agent is an upregulator of LDL receptor activity including MD-700.

26. The pharmaceutical combination according to claim 6 wherein, the hypolipidemic agent is a cholesterol absorption inhibitor including ezetimibe.

27. The pharmaceutical combination according to claim 6 wherein, the lipid-modulating agent is a cholesteryl transfer protein inhibitor selected from CP-529,414; SC-744; SC-795; CETi-1; and JTT-705.

28. The pharmaceutical combination according to claim 6 wherein, the hypolipidemic agent is an ileal Na$^+$/bile acid cotransporter inhibitor.

29. The pharmaceutical combination according to claim 6 wherein, the hypolipidemic agent is an ATP citrate lyase inhibitor.

30. The pharmaceutical combination according to claim 6 wherein, the lipid-modulating agents are selected from a phytoestrogen compound selected from isolated soy bean protein, soy protein concentrate, soy flour, isoflavone, genistein, daidzein, glycitein or equol, or phytosterols, phytostanol and tocotrienol; a beta-lactam cholesterol absorption inhibitor; an HDL upregulator selected from an LXR agonist, a PPAR ct-agonist and an FXR agonist; an LDL catabolism promoter; a sodium-proton exchange inhibitor; an LDL-receptor inducer; steroidal glycoside; an anti-oxidant selected from beta-carotene, ascorbic acid, ct-tocopherol, retinol, Vitamin C antihomocysteine agent, folic acid, a folate, Vitamin B6, Vitamin B12 and Vitamin E; isoniazid; a cholesterol absorption inhibitor; an HMG-CoA synthase inhibitor; a lanosterol demethylase inhibitor; a PPAR δ agonist for treating dyslipidemia; a sterol regulating element binding protein-I selected from a aphingolipid, ceramide, neutral sphingomyelenase or fragment thereof.

31. The pharmaceutical combination according to claim 6 wherein, the hypolipidemic agent is selected from pravastatin, lovastatin, simvastatin, atorvastatin, fluvastatin, pitavastatin, rosuvastatin, niacin and cholestagel.

32. A method for the treatment of bulimia or obesity which comprises administering to a mammalian species in need of treatment a therapeutically effective amount of a compound as defined in claim 1.

* * * * *

UNITED STATES PATENT AND TRADEMARK OFFICE
CERTIFICATE OF CORRECTION

PATENT NO.       : 7,517,900 B2  
APPLICATION NO.  : 10/959866  
DATED            : April 14, 2009  
INVENTOR(S)      : Annapurna Pendri et al.

Page 1 of 8

It is certified that error appears in the above-identified patent and that said Letters Patent is hereby corrected as shown below:

On the Title Page:

Item (56) References Cited, under OTHER PUBLICATIONS:

Column 2, Herrero reference, after "8589", insert -- , esp. page 8581 --.
The reference should read:
-- Herrero, et al., Tetrahedron, 58, 2002, 8581-8589, esp. page 8581.* --.

Column 2, Bicking reference, change "Diruetics" to -- Diuretics --.
The reference should read:
-- Bicking, J.B. et al., "Pyrazine Diuretics. III. 5- and 6-aminopyrazinecarboxamides",
J. Med. Chem., vol. 10, No. 4, pp. 598-602 (1967). --.

Column 2, Bonnet reference, change "if" to -- or --.
The reference should read:
-- Bonnet, V. et al., "Syntheses of substituted pyridines, quinolines and diazines via
palladium-catalyzed cross-coupling of aryl Grignard reagents", Tetrahedron, vol. 58,
pp. 4429-4438 (2002). --.

In the Claims:

Claim 1:
Column 74, line 10, change "-4-CN" to -- 4-CN --.
Column 74, line 14, change "provisos" to -- proviso --.

Claim 2:
Column 74, line 46, change "4-CN and" to -- and 4-CN; --.

Signed and Sealed this
Sixteenth Day of August, 2011

David J. Kappos
*Director of the United States Patent and Trademark Office*

CERTIFICATE OF CORRECTION (continued)
U.S. Pat. No. 7,517,900 B2

In the Claims:

Claim 3:

Column 74, line 62 to 65, change "  " to -- 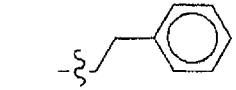 . --.

Column 75, lines 7 to 15, after " 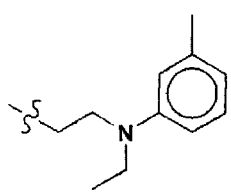 " insert -- , --.

Column 75, lines 41 to 43, change " 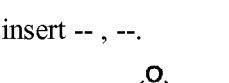 " to --  . --.

Claim 4:

Column 76, line 37 to 49, change " 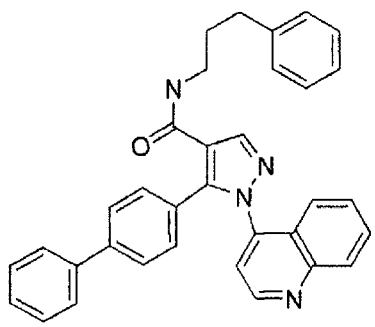 " to

-- 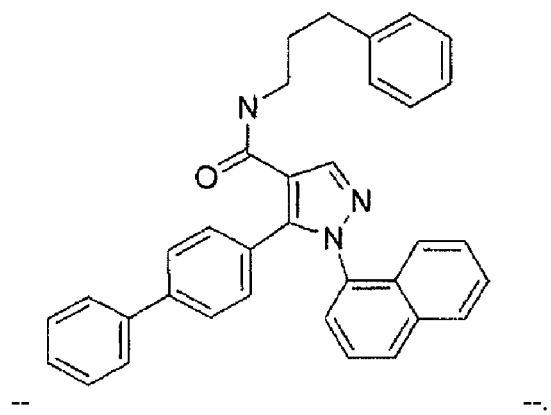 --.

CERTIFICATE OF CORRECTION (continued)
U.S. Pat. No. 7,517,900 B2

In the Claims:

Column 77, lines 1 to 16, change " 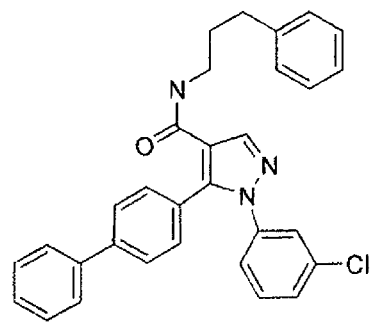 " to  --.

Column 77, lines 18 to 35, change " 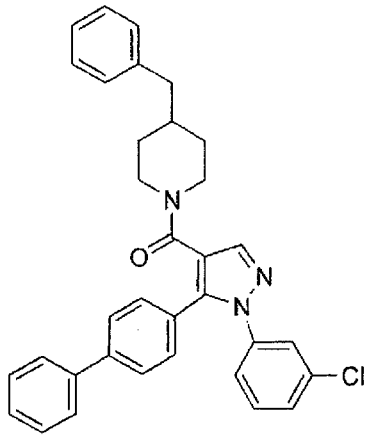 " to  --.

CERTIFICATE OF CORRECTION (continued)
U.S. Pat. No. 7,517,900 B2

In the Claims:

Column 78, lines 27 to 44, change " 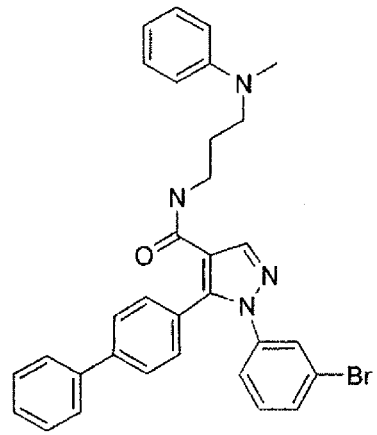 " to --  --.

CERTIFICATE OF CORRECTION (continued)
U.S. Pat. No. 7,517,900 B2

Page 5 of 8

In the Claims:

Column 78, lines 49 to 66, change " 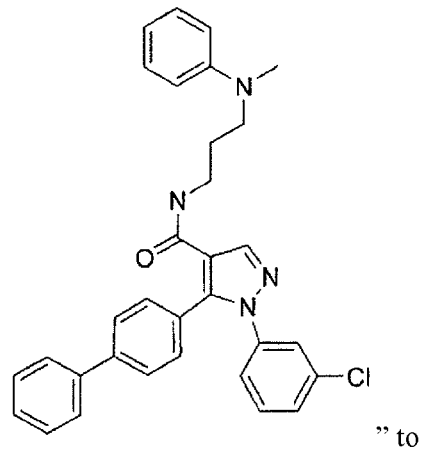 " to 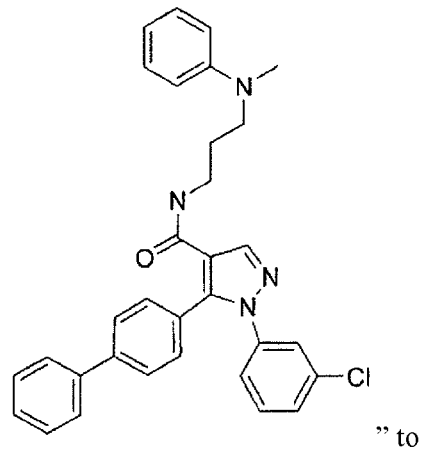

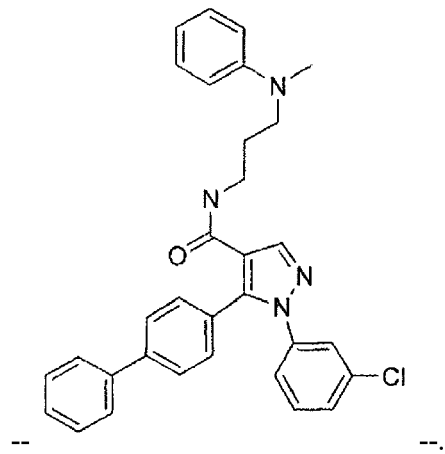

-- --.

CERTIFICATE OF CORRECTION (continued)
U.S. Pat. No. 7,517,900 B2

In the Claims:

Column 79, lines 1 to 18, change " 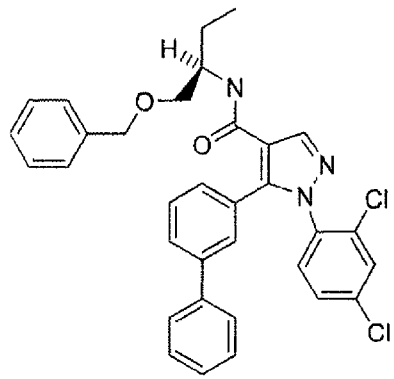 " to 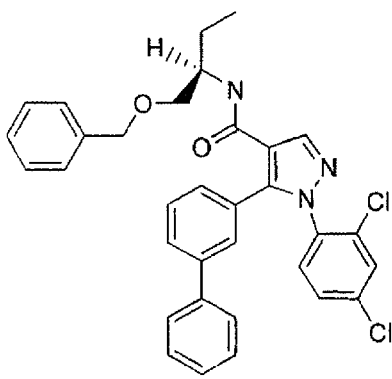 --.

In the Claims:

CERTIFICATE OF CORRECTION (continued)
U.S. Pat. No. 7,517,900 B2

Column 79, lines 20 to 33, change " 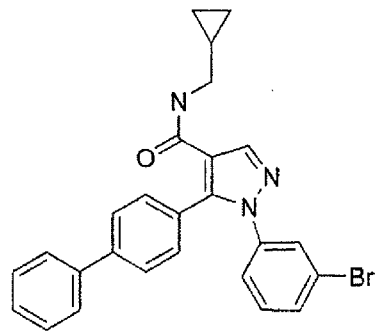 " to

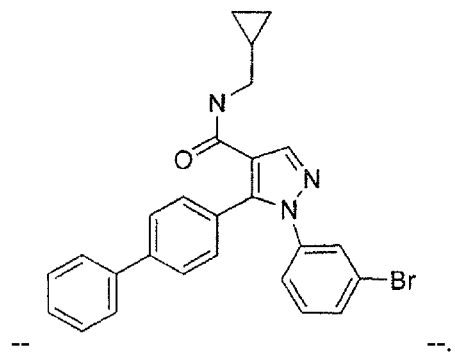

-- --.

Column 79, line 51 to 66, change " 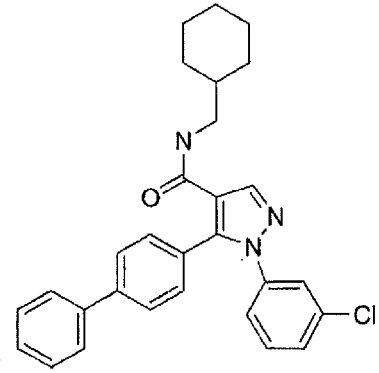 " to

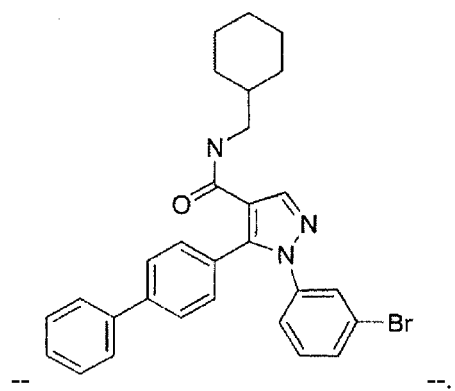

-- --.

In the Claims:

Claim 8:
    Column 81, line 23, change "chiorphentermine" to -- chlorphentermine --.

Claim 13:
    Column 81, line 57 and 58, change "chiorpropamide" to -- chlorpropamide --.

Claim 17:
    Column 82, line 6, change "PPARγ" to -- PPAR γ --.

Claim 19:
    Column 82, line 14, change "PPARα/γ" to -- PPAR α/γ --.

Claim 20:
    Column 82, line 28, change "dichioroacetate" to -- dichloroacetate --.

Claim 21:
    Column 82, line 40, change "phosphinyiphosphonates" to -- phosphinylphosphonates --.

Claim 23:
    Column 82, line 50, change "Policexide" to -- Polidexide --.
    Column 82, line 52, change "istigmastanylphos-phorylcholine" to
-- stigmastanylphosphorylcholine --.

Claim 30:
    Column 84, line 1, change "ct-agonist" to -- α-agonist --.
    Column 84, line 4, change "ct-tocopherol" to -- α-tocopherol --.
    Column 84, line 10, change "aphingolipid, ceramide, neurtal sphingomyelenase" to
-- sphingolipid, ceramide, neurtal sphingomyelinase --.